United States Patent [19]

Lin

[11] Patent Number: 5,278,176
[45] Date of Patent: Jan. 11, 1994

[54] NICOTINE DERIVATIVES THAT ENHANCE COGNITIVE FUNCTION

[75] Inventor: Nan-Horng Lin, Mundelein, Ill.

[73] Assignee: Abbott Laboratories, Abbott Park, Ill.

[21] Appl. No.: 933,458

[22] Filed: Aug. 21, 1992

[51] Int. Cl.$^5$ .................... C07D 401/04; A61K 31/44
[52] U.S. Cl. ...................... 514/343; 546/281; 546/282
[58] Field of Search ............... 546/281, 282; 514/343

[56] References Cited

U.S. PATENT DOCUMENTS 4,332,945  6/1982  Edwards ........................... 546/281

FOREIGN PATENT DOCUMENTS 62-81381  4/1987  Japan .

OTHER PUBLICATIONS

Murphy J. Biol. Chem. 1973, 248, 2796–800.
Clark et al. Principles of Psychopharmacology 1970 p. 166.
Rueppel et al. J.A.C.S. 1971, 93, 7021–8.
Merck Index Eleventh edition pp. 1281–1283.
Acheson et al. J. Chem. Soc. Perkin. Trans. 1980, 1: 579–85.
Wade J. R. Organic Chemistry p. 349, 1987.

*Primary Examiner*—Jane T. Fan
*Attorney, Agent, or Firm*—Richard A. Elder; Steven F. Weinstock; Edward H. Gorman, Jr.

[57] ABSTRACT

Selective and potent nicotinic agonists of the formula:

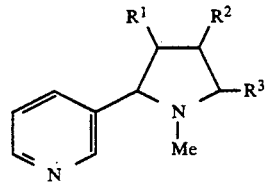

including pharmaceutically-acceptable salts or prodrugs thereof, useful in the treatment of dementias, attentional hyperactivity disorder, anxiety associated with cognitive impairment, or substance abuse withdrawal characterized by decreased cholinergic function.

8 Claims, 4 Drawing Sheets

NICOTINE DERIVATIVES THAT ENHANCE COGNITIVE FUNCTION

TECHNICAL FIELD

This invention relates to nicotine derivatives and pharmaceutical compositions thereof which are cholinergic agonists selective for neuronal nicotinic receptors, to methods for preparing these compounds, to synthetic intermediates employed in these processes and to a method of treating cognitive, neurological and mental disorders, such as dementias and anxiety, which are characterized by decreased cholinergic function, with such compounds. This invention also relates to a method of treating or preventing withdrawal symptoms caused by the cessation of chronic or long term use of tobacco products, as well as to a method of ameliorating the symptoms of anxiety and frustration associated with withdrawal of other addictive substances such as, for example, cocaine, diazepam or alcohol.

BACKGROUND OF THE INVENTION

Dementia has been widely recognized as a very serious health problem. Alzheimer's Disease, which has been identified by the National Institutes of Aging as accounting for more than 50% of dementia in the elderly is the fourth or fifth leading cause of death in Americans over 65 years of age. Four million Americans, 40% of Americans over age 85 (the fastest growing segment of the U.S. population), have Alzheimer's Disease. Twenty-five percent of all patients with Parkinson's Disease also suffer from Alzheimer's Disease-like dementia. And in about 15% of patients with dementia, Alzheimer's Disease and multi-infarct dementia coexist. The third most common cause of dementia, after Alzheimer's Disease and vascular dementia, is cognitive impairment due to organic brain disease related directly to alcoholism, which occurs in about 10% of alcoholics.

The precise molecular lesion(s) that contribute to the morphological and functional deficits associated with dementia is unclear despite intensive research efforts over the last decade. However, the most consistent abnormality for Alzheimer's Disease, as well as for vascular dementia and cognitive impairment due to organic brain disease related directly to alcoholism, is the degeneration of the cholinergic system arising from the basal forebrain (BF) to both the cortex and hippocampus (Bigl et al., in: *Brain Cholinergic Systems*, M. Steriade and D. Biesold, eds., Oxford University Press, Oxford, 1990, pp. 364-386). In particular, neurochemical evidence from the brains of patients afflicted with Alzheimer's Disease has revealed reliable decreases in markers of cholinergic neuronal function (Perry et al., *Br. Med. J.*, 1978, 2:1457; Reisine et al., *Brain Res.*, 1978, 159:477; Coyle et al., *Science*, 1983, 219:1184; McGeer et al., *Neurology*, 1984, 34:741). While there are a number of other neurotransmitter systems affected by Alzheimer's Disease (Davies, *Med. Res. Rev.*, 1983, 3:221), the relative occurrence of such abnormalities is less consistent or the effect is less profound than the decreases in these cholinergic neuronal function markers. More specifically, substantial reductions (30-50%) in nicotinic cholinergic receptors have been consistently reported in the brains of patients with Alzheimer's Disease and Parkinson's Disease (Keller et al., *Brain Res.*, 1987, 436:62; Whitehouse et al., *Neurol.*, 1988, 38:720), whereas changes in muscarinic cholinergic receptors are less remarkable and more dependent on receptor subtype.

However, degeneration of the cholinergic neurotransmitter system is not limited to individuals suffering from dementia. It has also been seen in healthy aged adults and rats. Decreases in cholinergic markers in the basal forebrain, decreases in cortical activities of the biosynthetic and degradative enzymes for acetylcholine, decreases in the ability to release acetylcholine from tissue slices, and decreases in numbers of cortical nicotinic receptors have all been reported in otherwise healthy aged individuals (for review, see Giacobini, *J. Neurosci. Res.* 1990, 27:548). Moreover, for those cholinergic neurons that remain, aging may cause a decrease in the temporal fidelity of existing impulse flow from the basal forebrain to the cortex (Aston-Jones et al., *Brain Res.*, 1985, 325:271). Consistent with these findings are pharmacological studies suggesting that cholinergic mechanisms are, at least in part, responsible for the memory disturbances in aged animals and humans not suffering from Alzheimer's Disease (Drachman and Leavitt, *Arch. Neurol.*, 1974, 30:113; Bartus et al., *Science*, 1982, 217:408).

Other clinical correlates associated with the neurodegenerative process of Alzheimer's Disease are decreases in regional cerebral blood flow and cerebral glucose utilization, which largely parallel the areas where cholinergic deficits occur (Ingvar and Risberg, *Exp. Brain Res.*, 1962, 3:195; Ingvar et al., *Aging: Alzheimer's Disease, Senile Dementia and Related Disorders*, Vol. 7, R. Katzman, R. D. Terry, and K. L. Bick, eds., Raven Press, 1978, p. 203; Dastur, *J. Cerebral Blood Flow & Metabol.*, 1985, 5:1). In fact, it has been suggested that routine measurement of cerebral blood flow may be a useful procedure in evaluating patients suspected of having dementia, and of Alzheimer's Disease in particular.

Conflicting reports exist regarding the effect of aging on resting cerebral blood flow and cerebral glucose utilization in "normal healthy" aged humans (Dastur, *J. Cerebral Blood Flow & Metabol.*, 1985, 5:1,) and rats (Smith et al., *Brain*, 1980, 103:351; Buchweitz-Milton and Weiss, *Neurobiol. Aging*, 1987, 8:55). Although decreases in cerebral blood flow and cerebral glucose utilization are generally reported in aged populations, it has been suggested that these decreases are secondary to other ongoing cerebral dysfunctions. Nonetheless, deficiencies in metabolic and cerebrovascular responses to pharmacologic and physiologic perturbation are consistently reported. Of particular interest is the recent finding in rats that increases in cerebral blood flow elicited by electrical stimulation of the basal forebrain shows age-related impairments (Linville and Arneric, *Soc. Neurosci. Abstract.*, 1989, 15:175). Indeed, studies that compare the degree of learning impairment with the degree of reduced cortical cerebral blood flow in aged rats show a good correlation (Berman et al., *Neurobiol. Aging*, 1988, 9:691).

Chronic alcoholism, more particularly, the resultant organic brain disease, like Alzheimer's Disease and normal aging, is also characterized by diffuse reductions in cortical cerebral blood flow in those brain regions where cholinergic neurons arise (basal forebrain) and project to (cerebral cortex) (Lofti & Meyer, *Cerebrovasc. and Brain Metab. Rev.*, 1989, 1:2). Moreover, of all the neurotransmitter systems studied, the neurotoxic effects of alcohol on the cholinergic system are thought to be the most important.

Recent clinical evidence suggests that the characteristic perfusion abnormality observed in Alzheimer's Disease patients reflects regional nicotinic cholinergic deficits (Prohovnik, *Neurobiol. Aging*, 1990, 11:262). In particular, mecamylamine, a centrally-acting nicotinic receptor antagonist, reduces resting cortical perfusion in the parietotemporal cortex of humans, the area of the cortex most consistently found to be impaired in functional brain imaging of Alzheimer's Disease patients. In agreement with this finding, regulation of cerebral blood flow in the frontoparietal cortex, governed by the basal forebrain, is also dependent upon nicotinic mechanisms in the rat (Arneric, *J. Cerebral Blood Flow & Metabol.*, 1989, 9(Suppl. 1): S502).

Intuitively, regardless of specific etiologic process, therapies directed towards enhancing cognitive processing would be contingent upon maintaining a well-regulated balance between adequate cerebral blood flow, cerebral glucose utilization and cholinergic neurotransmission arising from the basal forebrain.

Pilot clinical studies suggest that nicotine may be useful for the acute treatment of deficits in attention and information processing associated with Alzheimer's Disease (Sahakian et al., *Brit. J. Psych.*, 1989, 154:797; Newhouse et al., *Psychopharmacol.*, 1988, 95:171). Anecdotal evidence suggests a negative correlation between Alzheimer's Disease and smoking, and both acutely and chronically-administered nicotine enhances cognitive function in rats (Levin et al., *Behav. Neural Biol.*, 1990, 53:269), an effect that is preserved in aged animals (Cregan et al., *Soc. Neurosci. Abstract*, 1989, 15:295). These clinical findings are supported by animal studies demonstrating a neurogenerative/neuroprotective action of chronically-administered nicotine on both neuronal and vascular functions following hemitransection or MPTP-induced destruction of the nigro-striatal dopamine system (Janson et al., *Prog. Brain Res.*, 1989, 79:257; Owman et al., *Prog. Brain Res.*, 1989, 79:267). Interestingly, in contrast to the classical down-regulation of receptors typically seen with receptor agonists, chronic nicotine administration up-regulates (50–100%) the number of receptors without affecting affinity (Benwell et al., *J. Neurochem.*, 1988, 50:1243). This effect occurs both in humans and smaller animals such as rats (Lapchack et al., *J. Neurochem.*, 1989, 52:483).

Existing cholinergic agonists, however, are therapeutically sub-optimal. This is due to unfavorable pharmacokinetics (e.g., with arecoline and nicotine), poor potency and lack of selectivity (e.g., with RS-86), poor CNS penetration (e.g., with carbachol) or poor oral bioavailability (e.g., with nicotine). RS-86, for example, has similar affinity for cholinergic receptors located in the heart and cortical tissues and is a full agonist at cardiac receptors, whereas it is only a partial agonist at cortical receptors (S. B. Freedman, *British Journal of Pharmacology*, 1986, 87:29P). In addition, known agents have many unwanted central agonist actions, including hypothermia, hypolocomotion and tremor and peripheral side effects, including miosis, lacrimation, defecation and tachycardia (Benowitz et al., in: *Nicotine Psychopharmacology*, S. Wonnacott, M. A. H. Russell, & I. P. Stolerman, eds., Oxford University Press, Oxford, 1990, pp. 112–157; M. Davidson, et al, in *Current Research in Alzheimer Therapy*, E. Giacobini and R. Becker, eds.; Taylor & Francis: New York, 1988; pp 333–336).

In addition to treating decline in cognitive ability by improving cholinergic function and cerebral blood flow, it is also desirable to symptomatically treat the mental disorders accompanying the earlier stages of Alzheimer's Disease. Anxiolytics have been used to treat the severe agitation that most Alzheimer's patients experience with the initial loss of memory (IN-PHARMA, Mar. 16, 1991, pg 20). In fact, the use of anxiolytics has become an important aspect of treatment strategies for Alzheimer's Disease (Schmidt et al., *Drug Dev. Res.*, 1988, 14:251). Nicotine is known to have anxiolytic properties (Pomerleau et al., *Addictive Behaviors*, 1984, 9:265) and, therefore, nicotine or selective nicotine agonists may be useful in the treatment of the anxiety associated with dementias, such as Alzheimer's Disease.

Others situations where beneficial therapeutic outcome may be achieved or improved through administration of nicotine or a nicotine agonist, because of the anxiolytic properties of these agents, include attentional deficit disorder and drug withdrawal.

Attention-deficit disorder (ADD), with or without hyperactivity, is a behavioral disorder characterized by distractibility and impulsiveness. Children with this disorder are handicapped by their inability to concentrate and control their impulsivity, especially in settings requiring sustained attention, for example, in school. While a cure for this disorder has not been found, stimulants, such as pemoline, have been used successfully in management of the behavorial manifestations of ADD. Nicotine, because of its ability to improve concentration and task performance (F. T. Etscorn, U.S. Pat. No. 4,597,961, issued Jul. 1, 1986; D. M. Warburton and K. Wesnes in *Smoking Behavior*, R. E. Thornton, ed., Churchill-Livingston, Edinburgh, 1978, pp. 19–43) is potentially useful in treating ADD.

Tobacco use, especially cigarette smoking, has long been recognized as a major factor leading to disease and death. Approximately 4,000 by-products of combustion, many of which are known carcinogens, have been found in cigarette smoke. Of the three most-studied constituents of cigarette smoke, two, tars and carbon monoxide, have been found to cause or exacerbate numerous life-threatening disorders. Tars are most often implicated in the induction of lung, larynx, oral cavity, esophageal and other cancers, and are also thought to be responsible for respiratory diseases, including pulmonary emphysema, chronic bronchitis and smokers respiratory syndrome. Carbon monoxide, on the other hand, combines with hemoglobin in the blood thereby decreasing the ability of the blood to carry oxygen and has been implicated as a causative agent in the development of coronary artery disease and arteriosclerosis. The third highly studied, and the most pharmacologically active substance, in tobacco products is nicotine, which is the reinforcing agent responsible for maintaining tobacco dependency (J. H. Jaffe in *Nicotine Pharmacology: Molecular, Cellular and Behavioral Aspects*, S. Wonnacott, M. A. H. Russell and I. P. Stolerman, eds., Oxford Science Publications, Oxford, 1990, pp. 1–37).

The nicotine withdrawal syndrome associated with smoking cessation is characterized by craving for nicotine, irritability, frustration or anger, anxiety, difficulty concentrating, restlessness, decreased heart rate and increased appetite or weight gain. Nicotine has, not surprisingly, been found to ease the withdrawal experienced by those attempting to break tobacco dependencies. As early as 1942, Johnston reported (L. Johnston, Lancet, 1942, 2:742) that injections of nicotine relieved the withdrawal symptoms experienced by cigarette smokers when they stopped smoking. More recently, in double-blind studies, nicotine was far superior to placebo in suppressing or preventing the appearance of many of the signs and symptoms of withdrawal (J. R. Hughes et al., *Psychopharmacology*, 1984, 83:82-7; N. G. Schneider et al., *Addictive Behavior*1984, 9:149-56; R. J. West et al., *Journal of Addiction*1984, 79:215-9; K. O. Fagerstrom in: *Nicotine Replacement: a Critical Evaluation*, O. F. Pomperleau and C. S. Pomperleau, eds., Alan R. Liss, Inc., New York, 1988, pp. 109-28; J. E. Henningfield and D. R. Jasinski, ibid, pp. 35-61). Irritability and impatience were reduced in at least five independent controlled studies, while anxiety and difficulty concentrating were reduced in at least two studies. Other symptoms for which nicotine was significantly more effective than placebo in at least one study include depression, hunger, somatic complaints, and sociability.

One approach to alleviating the symptoms of tobacco withdrawal has been to develop more efficient methods of delivering nicotine, itself, for example, in transdermal patches (F. T. Etscorn, U.S. Pat. No. 4,597,961, issued Jul. 1, 1986). The major problem with this approach is the non-selective effects of nicotine and in particular, the stimulant effects of increasing cardiac workload and oxygen demand that nicotine has on the heart. A selective nicotine agonist would be expected to be equally efficacious in relieving withdrawal symptoms with fewer cardiovascular liabilities.

Withdrawal from addictive substances in general, regardless of which particular agent is withdrawn, is a traumatic experience characterized by anxiety and frustration. These emotional disturbances contribute to failure in therapy and, consequently, to a return to substance dependence. Although ameliorating these symptoms does not eliminate the craving for the withdrawn drug, improving the individual's ability to cope and to concentrate should vastly improve the chances of successfully completing treatment. Nicotine has been found to be effective in reducing anger, irritability, frustration and feelings of tension, while increasing ability to focus upon the completion of tasks, without causing general response depression, drowsiness or sedation (R. R. Hutchinson et al., U.S. Pat. No. 3,879,794, issued Mar. 11, 1975).

It has now been discovered that compounds according to this invention are selective and potent nicotinic agonists useful in treating these problems.

No syntheses of fluorine-containing derivatives of nicotine have been reported. Acheson et al. have reported the preparation of 3'-bromonicotine (*J. Chem. Soc. Perkin Trans.*, 1980, 1:579-85). Murphy reported that the 5'-cyanonicotine is a metabolite of nicotine (*J. Biol. Chem.*, 1973, 248:2796-800), and Osdene et al. report that the compound has insecticidal activity (U.S. Pat. No. 4,093,620), but their disclosures cannot reasonably be said to suggest or anticipate the compounds of the present invention.

The syntheses of certain other substituted nicotine derivatives have been reported. For example, Shibagaki et al. (Japanese published application 62081381) describe various 5'-alkyl-substituted nicotine compounds which were synthesized for the purposes of "tobacco-related medical research". Edwards (U.S. Pat. Nos. 4,332,945 and 4,452,984) reports the synthesis of various 4'-substituted nicotine compounds with insecticidal activity. Still other nicotine compounds have been synthesized for reference purposes or in novel synthetic organic efforts (cf., Rueppel et al., *J Amer. Chem Soc.*, 1971, 93:7021-8; Cushman et al., *J. Org. Chem.*, 1972, 37:1268-71). None of the cited references, however, can be reasonably said to suggest or anticipate the compounds of the present invention, nor the use of these compounds as nicotinic agonists.

SUMMARY OF THE INVENTION

The present invention relates to novel nicotinic agonists of the formula:

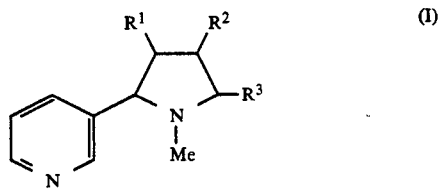

and pharmaceutically-acceptable salts or prodrugs thereof, and to pharmaceutical compositions comprising, and the use of these and similar compounds, and pharmaceutically-acceptable salts or prodrugs thereof, for treating cognitive, neurological and mental disorders, which are characterized by decreased cholinergic function in humans and lower mammals.

DETAILED DESCRIPTION OF THE INVENTION

Figure 1:
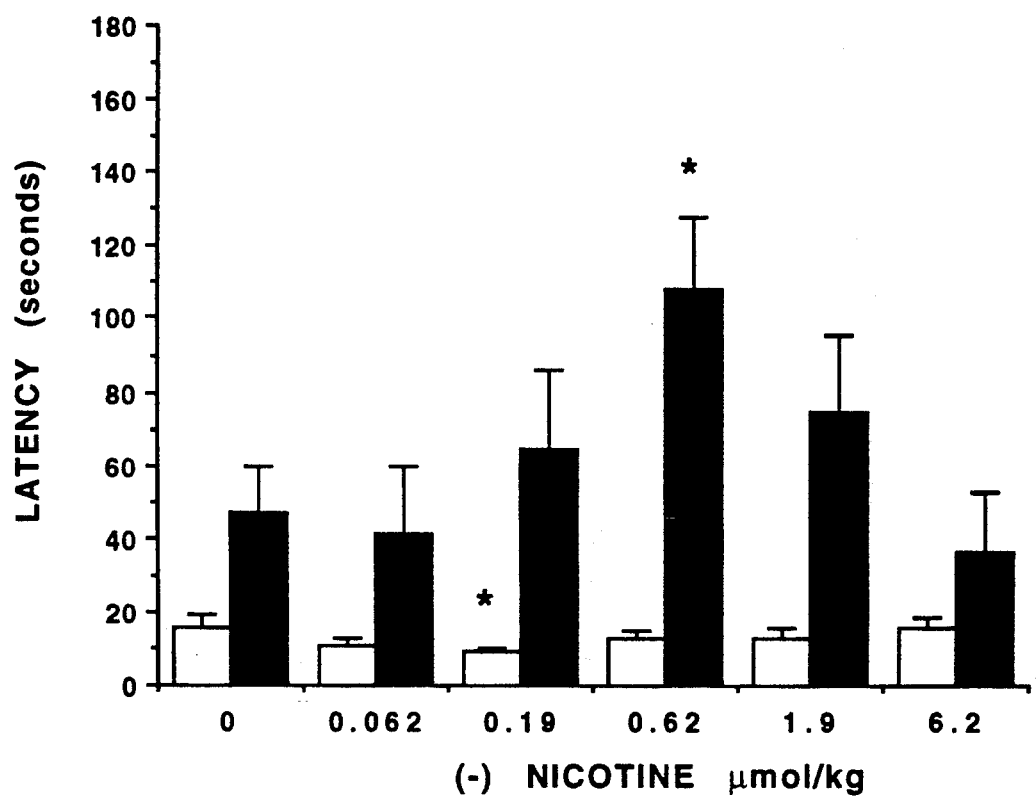
FIG. 1 is a graphical representation (bar graph) of the effects of (−) nicotine (0.01-1.0 mg/kg) on the performance of CD1 mice in Inhibitory Avoidance Studies expressed as median step-through latency time (seconds).

The present invention is directed novel nicotine derivatives which are selective and potent agonists at neuronal nicotinic acetylcholine receptors. These compounds, therefore, may be used in the treatment of cognitive, neurological and mental disorders characterized by decreased cholinergic function, such as, for example, dementias, attentional hyperactivity disorder and anxiety associated with cognitive impairment, as well as substance abuse withdrawal.

These selective and potent novel nicotinic agonists are represented by formula (I):

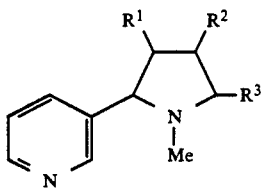

including pharmaceutically-acceptable salts or prodrugs thereof,
wherein:
$R^1$ is
  hydrogen,
  fluorine,
  fluoromethyl, as defined below,
  cyanomethyl, or
  cyano;
$R^2$ is
  hydrogen,
  fluorine,
  fluoromethyl,
  fluorobenzyl, as defined below,
  cyanomethyl, or
  cyano;
$R^3$ is
  hydrogen, or
  fluoromethyl;
with the requirement that not all of $R^1$, $R^2$ and $R^3$ are concurrently hydrogen.

Preferred embodiments of the present invention are represented by compounds of formula (I), wherein $R^1$ and $R^2$, or $R^2$ and $R^3$, or $R^1$ and $R^3$ are hydrogen, and $R^3$, $R^1$ or $R^2$, respectively is not hydrogen, but is otherwise as defined above.

The following are representative of the novel compounds of the present invention:
4'-Fluoronicotine,
4'-Fluoromethylnicotine,
3'-Fluoromethylnicotine,
4'-Cyanonicotine,
4'-Cyanomethylnicotine,
5'-Fluoromethylnicotine,
and pharmaceutically-acceptable salts and prodrugs thereof.

Particularly preferred novel compounds of the present invention include:
4'-Fluoronicotine, and
4'-Fluoromethylnicotine,
and pharmaceutically-acceptable salts and prodrugs thereof.

In another aspect of the present invention is provided the use as nicotinic agonists of formula (II):

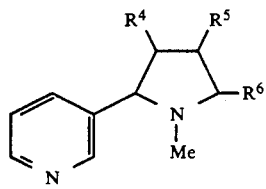

and pharmaceutically-acceptable salts or prodrugs thereof,
wherein:
$R^4$ is selected from the group consisting of:
  hydrogen,
  $C_1$–$C_6$-alkyl, as defined below,
  amino,
  $C_1$–$C_4$-acylamino, as defined below,
  hydroxyl, and
  hydroxymethyl;
$R^5$ is selected from the group consisting of:
  hydrogen,
  $C_1$–$C_6$-alkyl,
  $C_1$–$C_4$-alkoxy, as defined below,
  $C_1$–$C_4$-acyloxy, as defined below,
  methylsulfonyloxy,
  amino,
  aminomethyl;
  $C_1$–$C_4$-acylamino,
  thiocyanatomethyl,
  mercaptomethyl
  hydroxyl, and
  hydroxymethyl;
$R^6$ is selected from the group consisting of:
  hydrogen,
  $C_1$–$C_6$-alkyl,
  cyanomethyl,
  hydroxyl, and
  hydroxymethyl;
with the requirement that at least one, but not all, of $R^4$, $R^5$ and $R^6$ must be hydrogen at all times.

The present invention is also directed to pharmaceutical compositions comprising a therapeutically-effective amount of a compound of formula (I) or formula (II) and a pharmaceutically-acceptable carrier or diluent.

Preferred compounds of the present invention useful as nicotinic agonists are those represented by formula (II), wherein $R^4$ and $R^5$, or $R^4$ and $R^6$, or $R^5$ and $R^6$ are hydrogen, and the third substituent in each case is not hydrogen.

The following are representative of compounds having novel use as nicotinic agonists:
4'-Hydroxynicotine,
4'-Methylnicotine,
4'-Ethylnicotine,
4'-Hydroxymethylnicotine,
3'-Methylnicotine,
5'-Methylnicotine, and
5'-Butylnicotine,
4'-Methoxynicotine,
4'-Benzylnicotine,
4'-Acetyloxynicotine,
3',4'-Dimethylnicotine,
3'-Aminonicotine,
4'-Methanesulfonyoxynicotine,
3'-Aminonicotine,
3'-Methylaminonicotine,
3'-Fluoro-4'-methoxynicotine
3',4'-Difluoronicotine
4'-Fluoro-3'-fluoromethylnicotine
4',4'-Difluoronicotine
4'-Thiomethylnicotine,
4'-Thiocyanatomethylnicotine,
5'-Cyanonicotine,
3',5'-Dimethylnicotine,
4',5'-Dimethylnicotine,
4'-Fluoromethyl-3'-methylnicotine,
3'-Fluoromethyl-4'-methylnicotine, and
5'-Fluoromethyl-4'-methylnicotine.
and pharmaceutically-acceptable salts and prodrugs thereof.

Particularly preferred compounds of the present invention having novel use as nicotinic agonists include:

3',4'-Dimethylnicotine,
4'-Hydroxynicotine,
4'-Methylnicotine,
3'-Methylnicotine,
and pharmaceutically-acceptable salts and prodrugs thereof.

In yet another aspect of the present invention is provided a method of treating cognitive, neurological and mental disorders, which are characterized by decreased cholinergic function in humans and lower mammals, by administration of a compound of formula (I) or formula (II).

The term "acylamino" refers to an amino group protected with an acyl group, wherein a carbonyl group is attached to a $C_1-C_6$-alkyl group.

The term "acyloxy" refers to a hydroxy group protected with an acyl group, wherein a carbonyl group is attached to a $C_1-C_6$-alkyl group.

The term "alkyl" refers to branched or straight-chain alkyl groups of the size indicated, unsubstituted or substituted with 1-to-3 halogens or with one $C_1-C_4$-alkoxy or $C_1-C_4$-thioalkoxy substituent. Representatives of these compounds include, but are not limited to, methyl, ethyl, n-propyl, isopropyl, n-butyl, t-butyl, neopentyl, n-hexyl, methoxymethyl, thiomethoxymethyl, trifluoromethyl, and the like.

The term "alkylamino" refers to a nitrogen atom linked by an amine bond to an unsubstituted alkyl group, as defined above, of the size indicated, for example, methylamino, ethylamino, n-propylamino, i-propylamino and the like.

The term "alkoxy" refers to an oxygen atom linked by an ether bond to an unsubstituted alkyl group, as defined above, of the size indicated, for example, methoxy, ethoxy, t-butoxy, and the like.

The term "fluorobenzyl" refers to a benzyl group substituted with 1-to-5 fluorine atoms, such as, for example, 4-fluorobenzyl, 2,4-difluorobenzyl, 2,4,6-trifluorobenzyl, pentafluorobenzyl, and the like.

The term "$C_3-C_7$-cycloalkyl" refers to a monocyclic saturated hydrocarbon ring containing three-to-seven carbon atoms in the ring.

The term "halo" or "halogen" as used herein refers to bromo (Br), chloro (Cl), and fluoro (F).

The term "phenyl" refers to an unsubstituted phenyl ring or a phenyl ring substituted with 1, 2 or 3 substituents independently selected from halogen, $C_1-C_4$-alkyl, $C_1-C_4$-alkoxy and $C_1-C_4$-alkylthio, or with one substituent selected from $C_1-C_4$-alkanoyl, di-$C_1-C_4$-alkylamino and methylenedioxy.

The term "thioalkoxy" refers to a sulfur atom linked by a thioether bond to an unsubstituted alkyl group, as defined above, of the size indicated, for example, thiomethoxy, thioethoxy, and the like.

Compounds of the invention which have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof. The terms "R" and "S" configuration used herein are as defined by IUPAC 1974 Recommendations for Section E, Fundamental Stereochemistry, *Pure Appl. Chem.*, 1976, 45: 13–30.

The compounds of the present invention may be synthesized as shown in reaction schemes I through V presented below using the reactions and techniques described in this section. The reactions are performed in a solvent appropriate to the reagents and materials employed are suitable for the transformation being effected. It is understood by those skilled in the art of organic synthesis that the functionality present on the heterocyclic ring and other portions of the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of nitrogen-protecting groups is well known in the art for protecting amino groups against undesirable reactions during a synthetic procedure and many such protecting groups are known, cf, for example, T. H. Greene, *Protective Groups in Organic Synthesis*, John Wiley & Sons, New York (1981).

In accordance with Scheme I, the commercially available trans-4-cotinine carboxylic acid is esterified with an appropriate alcohol, exemplified by methanol, in the presence of a suitable acid to give the compound of formula 2. The ester is selectively reduced with an appropriate hydride reducing agent, preferably sodium borohydride, to give the 4-hydroxymethylcotinine compound of formula 3. The alcohol function is reacted with methanesulfonyl chloride to form the compound of formula 4, which contains the mesylate grouping, a good leaving group. The fluoride compound of formula 5 is formed by displacing the mesylate group with fluoride anion, using preferably tetrabutylammonium fluoride. The ring carbonyl function is then reduced with a hydride or borane reducing compound, preferably $BH_3$ in THF, to give the desired substituted nicotine compound of formula 6. Optionally, the compound of formula 3 is reacted with phenoxythiocarbonylchloride to give compound 7, which is treated with tris(trimethylsilyl)silane to give the methyl derivative of formula 8. This compound is reduced by the $BH_3$/THF treatment referred to above to give the desired 3'-methylnicotine compound of formula 9.

Scheme I

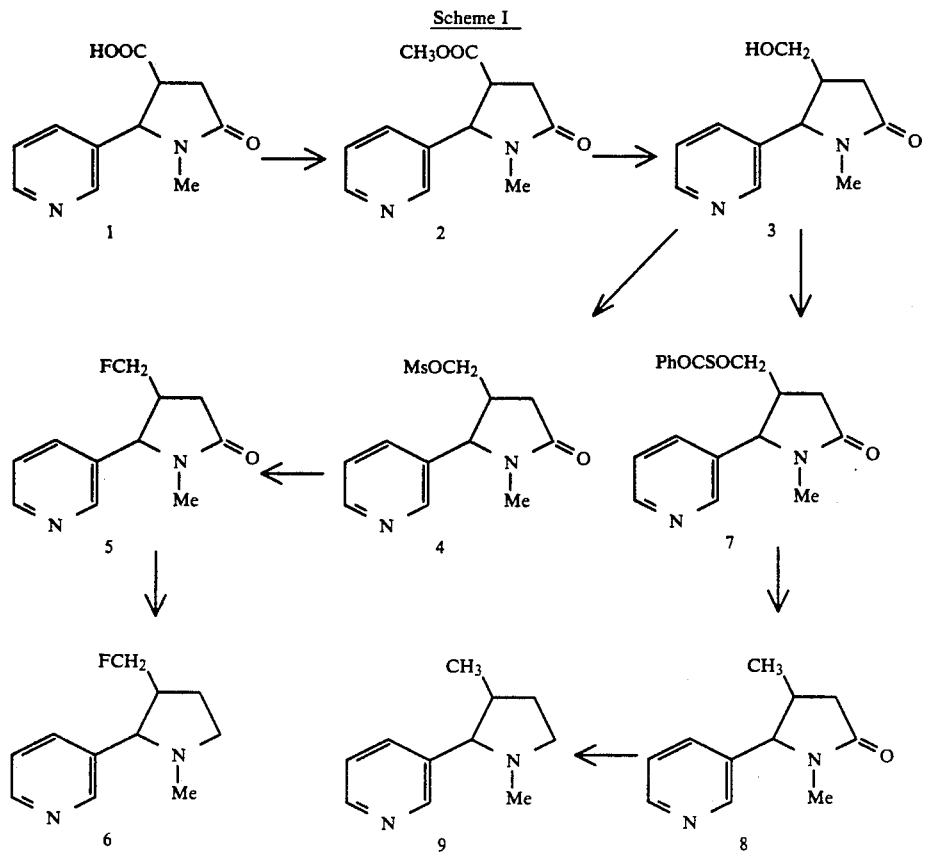

According to Scheme 2, various additional 3'-substituted nicotine compounds are formed. The starting carboxylic acid is converted to the amide of formula 10 by a two-step reaction, first forming the ester (compound 2 in Scheme 1), then reacting the ester with ammonia in a suitable solvent, such as THF for example. The dehydration of the amide to the nitrile of formula 11 is accomplished by treating the amide with PCl$_5$ in chloroform or methylene chloride at an elevated temperature. The desired 3'-cyanonicotine compound of formula 12 is formed by selectively reducing the cotinine compound of formula 11 using preferably trimethyloxonium tetrafluoroborate followed by reduction with sodium borohydride. By an alternate series of reactions the starting material (1) is converted to the benzyloxycarbonyaminocotinine (13) by reaction with DIA and DPPA. Reduction with borane in THF as described above gives the desired Cbz-aminonicotine (14). Removal of the Cbz group by hydrogenolysis gives the amine (18). This compound may be acylated by standard acylation procedures, such as reaction with acetic or propionic anhydride, or t-butyloxycarbonyl chloride or the like to give the desired acylaminonicotine compounds of formula 19. Alternately, compound (1) is converted by standard methods to give ketone compound (15). By means of a Bäyer-Villiger oxidation the ketone is converted into the ester (15a), for example the acetate ester when R is methyl. By a displacement reaction with fluoride ion, such as with sodium fluoride of tetrabutylammonium fluoride, the fluorocotinine compound (16) is prepared. Reduction with borane in THF as described above gives the desired 3'-fluoronicotine compound (17).

Scheme II

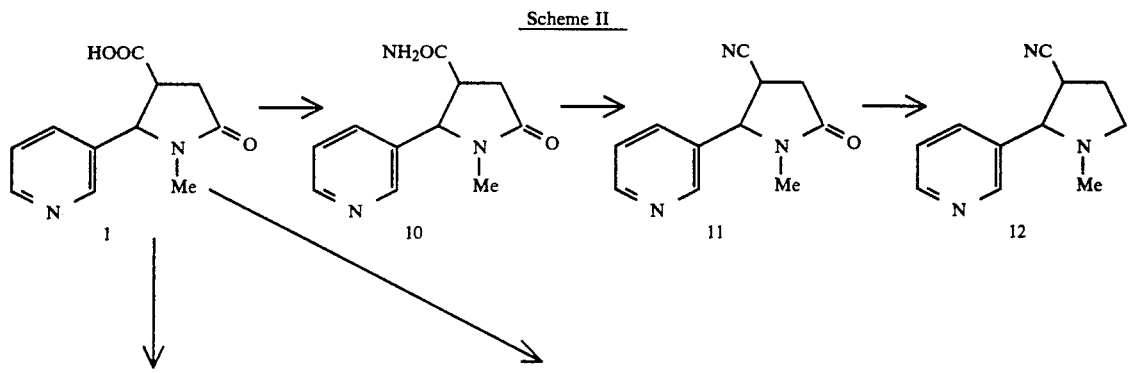

-continued
Scheme II

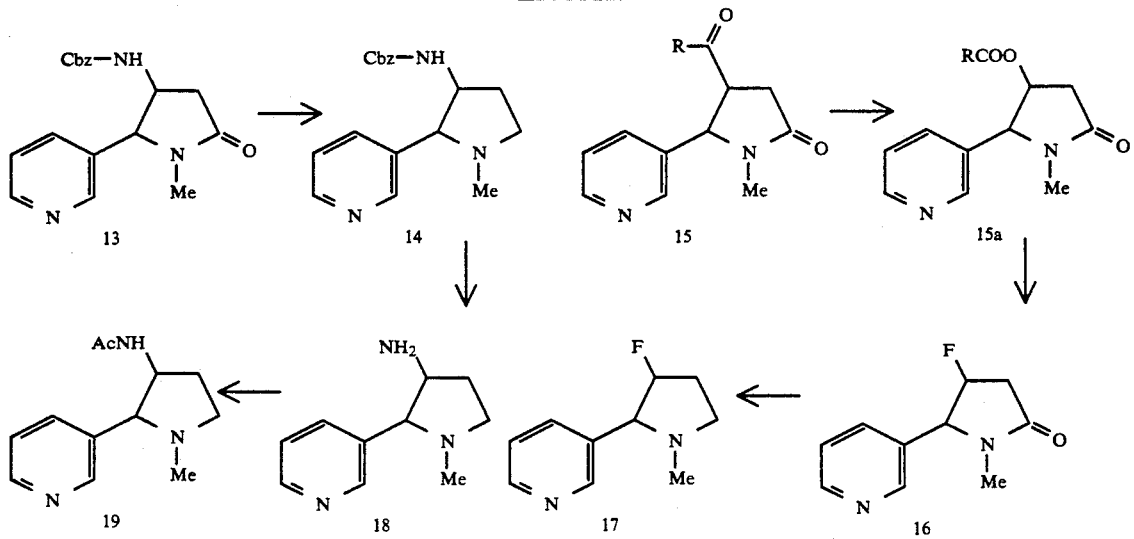

Various 4'-substituted nicotine compounds may be prepared by employing Scheme III. Cotinine (20) is reacted with lithium diisopropyl amide (LDA) at −78° C. followed by addition of oxaziridine and workup under acidic conditions to give the hydroxycotinine (21), which may be reacted with an alkylating reagent, such as methyl iodide or ethyl iodide, for example, to give the alkoxycotinine (22). This compound is reduced to the 4'-alkoxynicotine derivative with borane/THF as described in Scheme I. Alternately, the compound of formula 21 is treated with methanesulfonyl chloride to form the cotinine compound of formula 24, which is reduced with borane in THF to the nicotine derivative (25). The mesylate leaving group of the compound of formula 25 is optionally displaced with any of several groups. By displacement with sodium azide the azide compound (26) is formed, which upon reduction with lithium aluminum hydride or borane, for example, provides the 4'-aminonicotine derivative (27). Optionally, the amino group of (27) may be protected with an acyl protecting group as described for the acylation of compound (18) in Scheme II. When the leaving group of (25) is reacted with a fluoride compound, such as sodium fluoride or tetrabutylammonium fluoride, for example, the 4'-fluoronicotine derivative (28) is formed. When the leaving group of (25) is reacted with sodium cyanide, under basic conditions, the 4'-cyanonicotine compound (29) is prepared.

If, optionally, cotinine is reacted with lithium diisopropyl amide (LDA) at −78° C. followed by addition of formaldehyde, the hydroxymethyl cotinine (30) is prepared. Replacement of the hydroxyl function with the mesylate leaving group as described above provides compound (31), which is reduced to the nicotine compound (32) with borane in THF. The mesylate leaving group of the compound of formula 32 is optionally displaced with any of several groups. Displacement with fluoride as described above provides the 4'-fluoromethylnicotine compound of formula 33. Displacement with cyanide as described above provides the 4'-cyanomethylnicotine compound of formula 34. Displacement with thiocyanate ion, by treatment with sodium thiocyanate, for example, provides the thiocyanatomethylnicotine compound of formula 35. Displacement with a thiol (or substituted thiol, where R'=alkyl) provides the 4'-thiomethylnicotine or 4'-alkylthiomethylnicotine compound of formula 36.

Optionally, compound 20 is reacted with lithium diisopropyl amide (LDA) at −78° C. followed by addition of a fluorinated benzylbromide, for example, 4-fluorobenzyl bromide, 2-fluorobenzyl bromide, 2,4-fluorobenzyl bromide, or the like, to give the compound 30A, which upon reduction with borane/THF as described above gives the 4'-fluorobenzyl nicotine derivative of formula 30B.

5'-derivatives of nicotine are prepared in accordance with Scheme IV. Cotinine (20) is reacted with an alkyl lithium compound, in the cold (−78° C.) and in a suitable solvent, such as THF for example, to prepare the intermediate compound (37), which is treated immediately with sodium cyanoborohydride followed by workup in acid solution, such as hydrochloric acid, to provide the 5'-alkylnicotine compounds of formula 38 in a mixture of R and S isomers. Alternately, by reacting nicotine 5'-carboxylic acid of formula 39 (prepared as described by Hellmann, *Justus Liebigs Ann. Chem.* 672: 97–102 (1964)) with a suitable reducing agent,

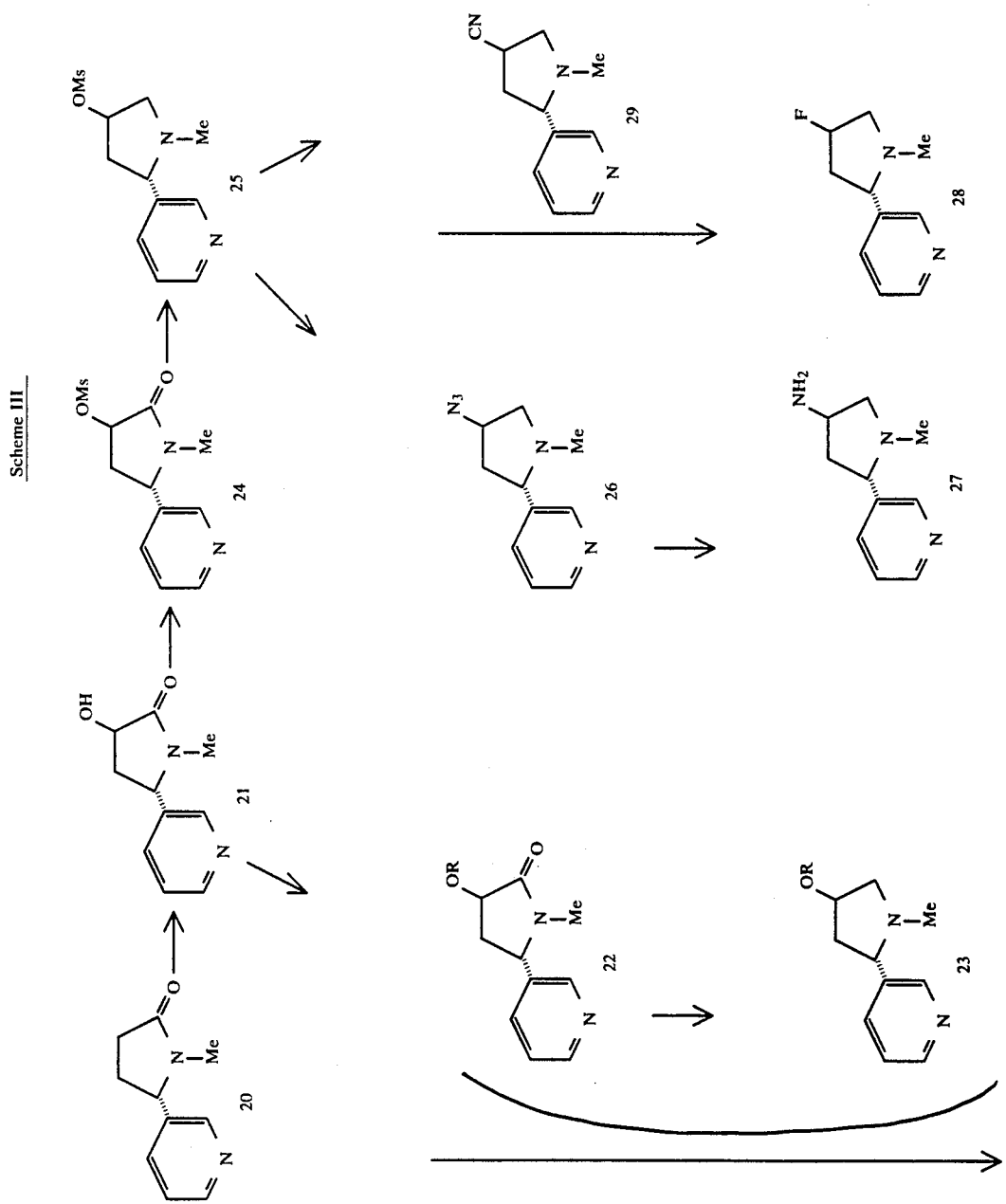

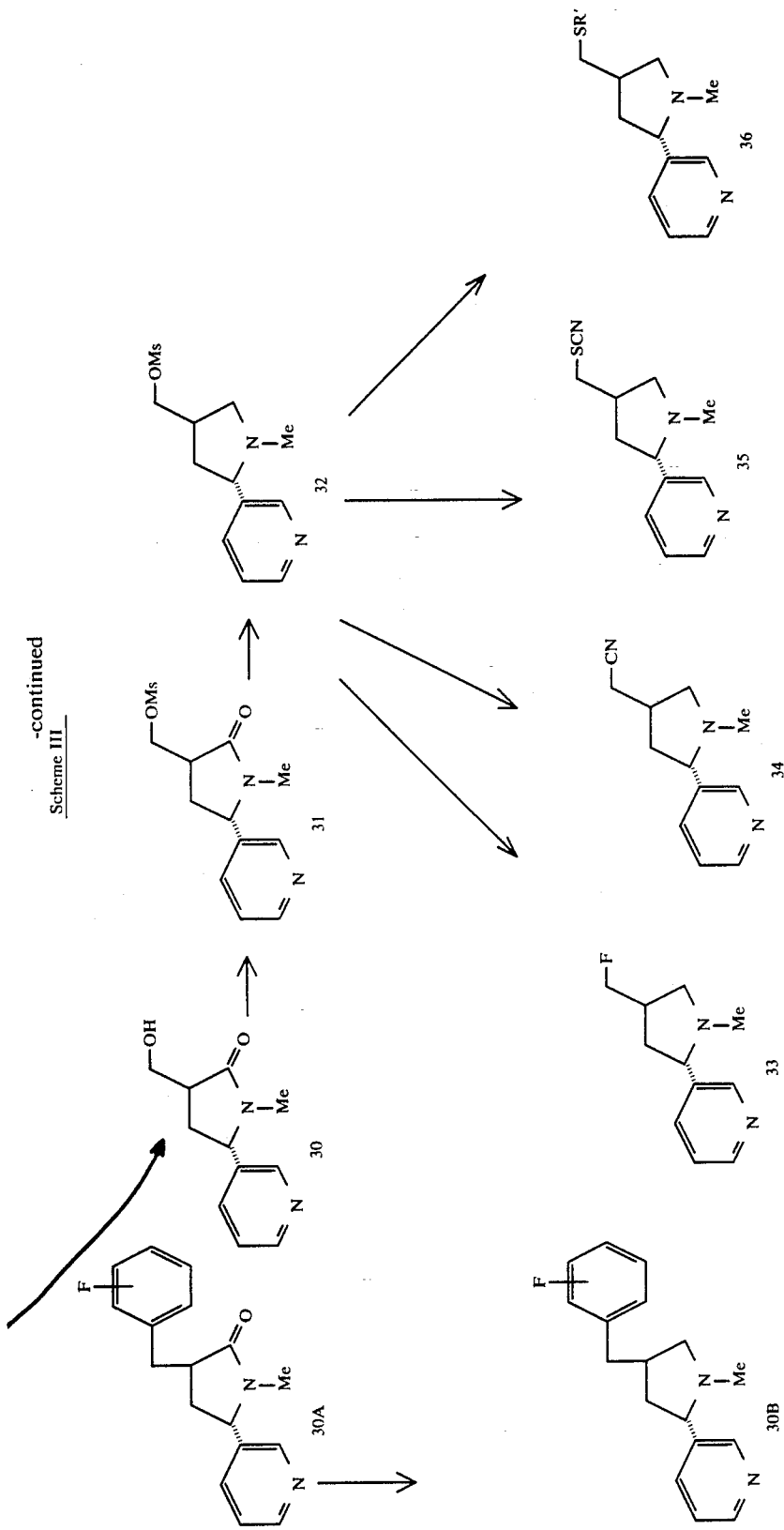

such as lithium aluminum hydride or another hydride reducing agent, for example, the 5'-hydroxymethylnicotine compound (40) is prepared. Treatment of the hydroxy compound with methanesulfonyl chloride provides the compound of formula 41, which possesses the mesylate leaving group. Displacement of the leaving group from compound (41) with fluoride ion as described above provides the 5'-fluoromethylnicotine compound of formula 42. Displacement of the leaving group from compound (41) with cyanide ion as described above provides the 5'-cyanomethylnicotine compound of formula 43.

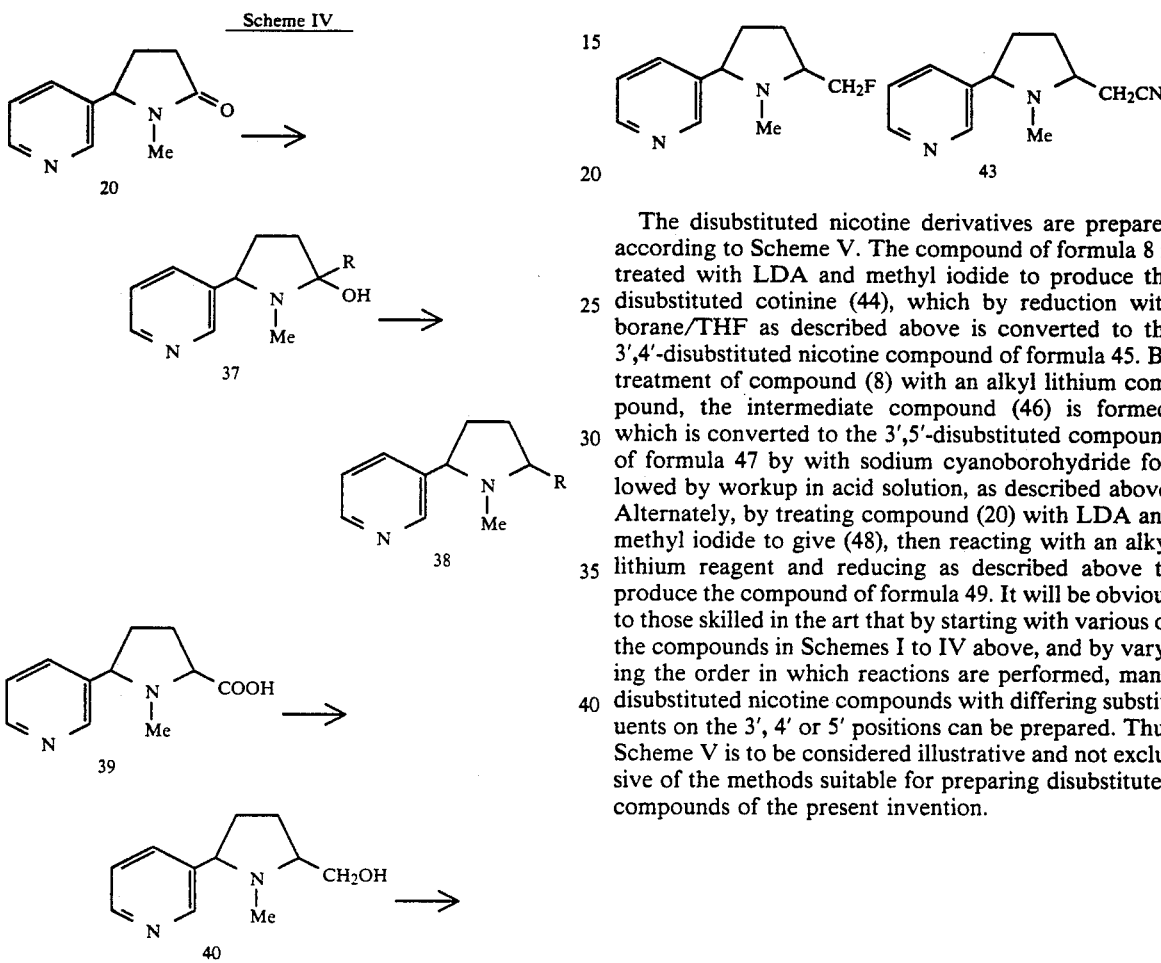

The disubstituted nicotine derivatives are prepared according to Scheme V. The compound of formula 8 is treated with LDA and methyl iodide to produce the disubstituted cotinine (44), which by reduction with borane/THF as described above is converted to the 3',4'-disubstituted nicotine compound of formula 45. By treatment of compound (8) with an alkyl lithium compound, the intermediate compound (46) is formed, which is converted to the 3',5'-disubstituted compound of formula 47 by with sodium cyanoborohydride followed by workup in acid solution, as described above. Alternately, by treating compound (20) with LDA and methyl iodide to give (48), then reacting with an alkyl lithium reagent and reducing as described above to produce the compound of formula 49. It will be obvious to those skilled in the art that by starting with various of the compounds in Schemes I to IV above, and by varying the order in which reactions are performed, many disubstituted nicotine compounds with differing substituents on the 3', 4' or 5' positions can be prepared. Thus Scheme V is to be considered illustrative and not exclusive of the methods suitable for preparing disubstituted compounds of the present invention.

Scheme V

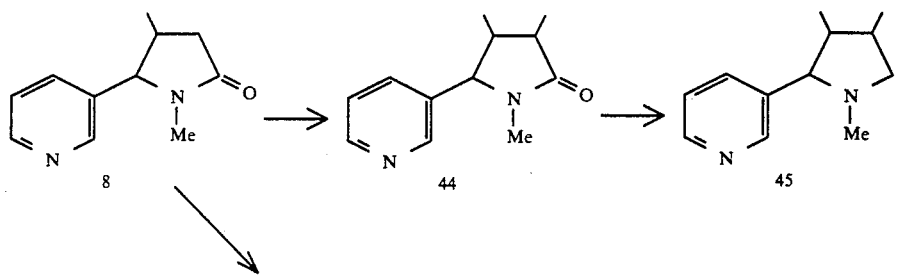

Scheme V

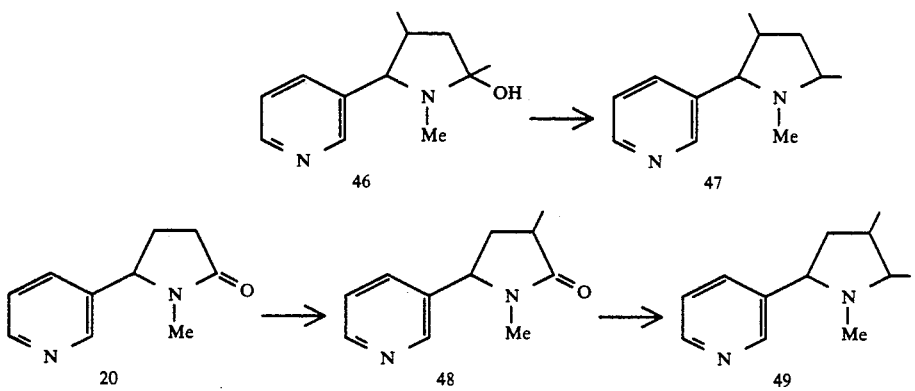

The compounds of the present invention may be used in the form of salts derived from inorganic or organic acids. These salts include but are not limited to the following: acetate, adipate, alginate, ascorbate, aspartate, benzoate, benzenesulfonate, bisulfate, borate, butyrate, camphorate, camphorsulfonate, citrate, cyclopentanepropionate, digluconate, dodecylsulfate, ethanesulfonate, fumarate, glucoheptonate, gluconate, glycerophosphate, hemisulfate, heptanoate, hexanoate, fumarate, hydrochloride, hydrobromide, hydroiodide, 2-hydroxyethanesulfonate, lactobionate, lactate, laurate, lauryl sulfate, maleate, methanesulfonate, nicotinate, 2-naphthalenesulfonate, oleate, oxalate, pamoate, palmitate, pectinate, persulfate, 3-phenylpropionate, phosphate, picrate, pivalate, propionate, stearate, succinate, sulfate, tartrate, thiocyanate, toluenesulfonate, undecanoate valerate salts and the like. Also, the basic nitrogen-containing groups may be quaternized with such agents as $C_1$–$C_6$-alkyl halides, such as methyl, ethyl, propyl, and butyl chlorides, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenylethyl bromides, and others. Water- or oil-soluble or dispersible products are thereby obtained.

The pharmaceutically acceptable salts of the present invention may be synthesized from the compounds of formula (I) by conventional chemical methods. Generally, the salts are prepared by treating the free amine with stoichiometric amounts or with an excess of the desired salt forming inorganic or organic acid in a suitable solvent or various combinations of solvents.

IN VITRO DETERMINATION OF NEURONAL NICOTINIC RECEPTOR BINDING POTENCIES AND SELECTIVITY

For the purpose of identifying compounds as cholinergic agonists which are capable of selectively interacting with nicotinic receptors in the brain, ligand-receptor binding assays were carried out as an initial screen. Initial screening indicated that the compounds of the present invention were effective at interacting with neuronal nicotinic receptors and they were, therefore, assayed for their ability (compared to (−)-nicotine) to label neuronal nicotinic receptors using [$^3$H]-methylcarbamylcholine ([$^3$H]-MCC) and for their ability (compared to (−)-nicotine) to compete with the selective muscarinic antagonist [$^3$H]-quinuclidinyl benzilate ([$^3$H]-QNB) for binding to muscarinic receptors.

The ability of the compounds of the invention to interact with cholinergic receptors and to act as cholinergic agonists can be demonstrated in vitro using the following protocols.

Protocols for Determination of Nicotinic Receptor Binding Potencies of Agonists Binding of [$^3$H]-methylcarbamylcholine ([$^3$H]-MCC) to nicotinic receptor was accomplished using crude synaptic membrane preparations from whole rat brain (Snyder and Enna, *Brain Research*, 1975, 100:81). Washed membranes were stored at −80° C. prior to use. Frozen aliquots were slowly thawed and resuspended in 20 volumes of buffer (containing: 120 mM NaCl, 5 mM KCl, 2 mM MgCl$_2$, 2 mM CaCl$_2$ and 50 mM Tris-Cl, pH 7.4 @4° C.). After centrifuging at 20,000 g for 15 minutes, the pellets were resuspended in 30 volumes of buffer. Homogenate (containing 125–150 μg protein) was added to triplicate tubes containing concentrations of test compound and [$^3$H]-MCC (3 nM) in a final volume of 500 μL. Samples were incubated for 60 minutes at 4° C., then rapidly filtered through Whatman GF/B filters presoaked in 0.5% polyethylimine using 3×4 mL of ice-cold buffer. The filters are counted in 4 mL of Ecolume ® (ICN). Nonspecific binding was determined in the presence of 10 μM (−)nicotine and values were expressed as a percentage of total binding. IC$_{50}$ values were determined with the ALLFIT nonlinear least squares curve-fitting program and IC$_{50}$ values were converted to Ki values using the Cheng and Prusoff correction (Ki=IC$_{50}$/(1+[ligand]/Kd of ligand). Alternately, data were expressed as a percentage of the total specific binding. The results are shown in Table 1.

These data suggest that the compounds of the present invention have high affinity for the neuronal nicotinic receptor, although they are slightly less potent than (−)nicotine. A number of the compounds of the present invention, however, both have more affinity for the neuronal nicotinic receptor than arecoline, a nicotinic agonist (Ki=59) that has demonstrated clinical utility.

N VIVO STUDIES DEMONSTRATING ACTIVITY AS COGNITION ENHANCERS

A. Inhibitory Avoidance Studies

The inhibitory (or sometimes called passive) avoidance (IA) test is a well accepted animal model of learning/memory used to assess the activity of novel muscarinic agonists to enhance cognitive function (Wanibuchi et al., Eur. J. Pharmacol., 1990, 187:479). Animals are placed in the illuminated (12×14×11 cm) portion of a two-chambered box, from which they enter through a guillotine door to the larger (24×13.5×12 cm) dark compartment of the box. Entry to the dark compartment is accompanied by a mild (0.5 mA), brief (2 seconds) footshock. Initial latencies to cross are recorded, with an imposed 60 second ceiling. Following a 72 hour retention interval, animals are returned to the illuminated chamber, and latency to return to the dark compartment is again recorded, with a ceiling of 180 seconds. No footshock is administered on the test day.

Figure 2:
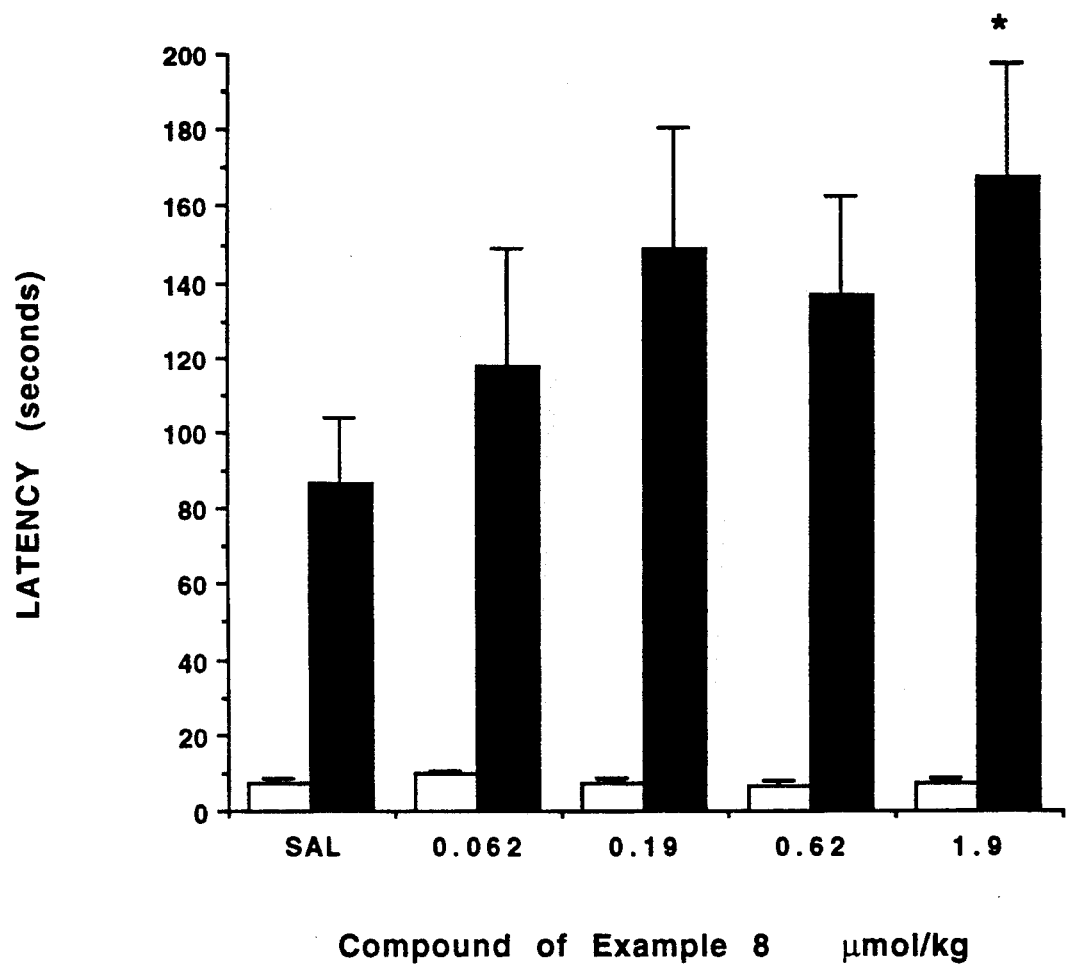
FIG. 2 is a graphical representation (bar graph) of the effects of the compound of Example 8 (0.001-1.0 mg/kg) on the performance of CD1 mice in Inhibitory Avoidance Studies expressed as median step-through latency time (seconds).
Figure 3:
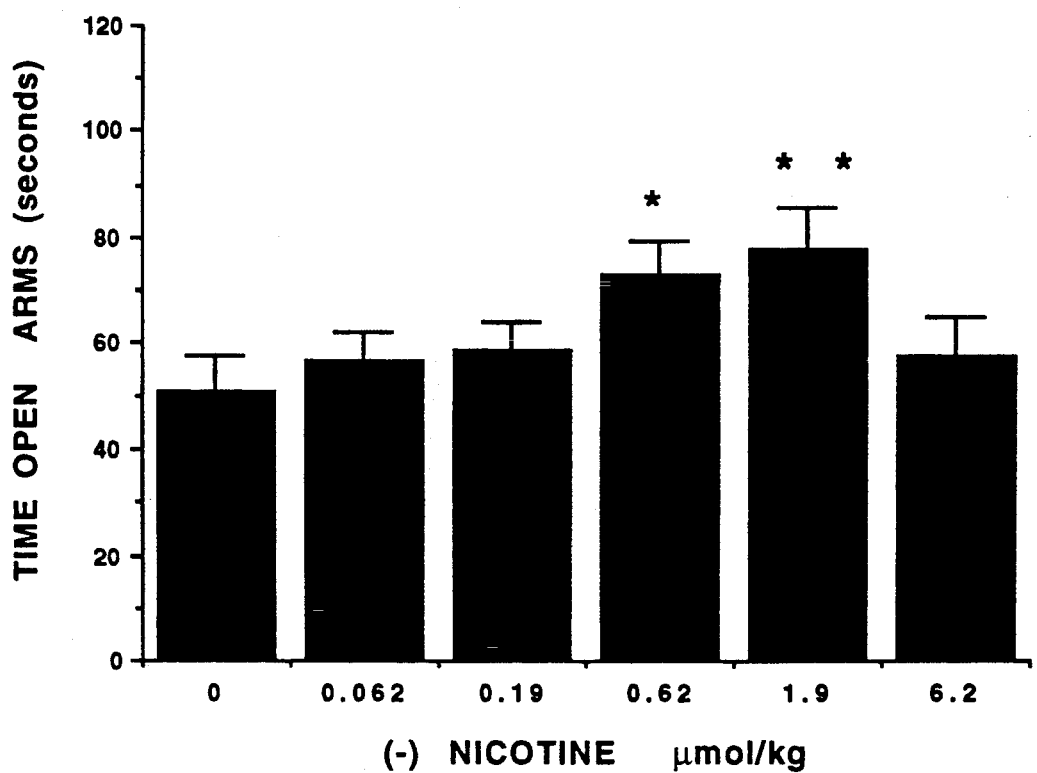
FIG. 3 is a graphical representation of the effects of (−) nicotine (0.01-1.0 mg/kg) on the performance of CD1 mice in the Elevated-Plus Maze Study expressed as median time (seconds) spent on the open arms of the maze.

Animals received systemic injections of (−)nicotine and the compound of Example 8 (0.06-6.2 μmol/kg, IP) 15 minutes before training in the inhibitory avoidance task, and retention was evaluated 24 hours later. Twelve animals were used in each group. FIG. 1 demonstrates that (−)nicotine induced a dose-dependent facilitation of retention of the avoidance response at 0.62 μmol/kg (p<0.05). The compound of Example 8 also significantly facilitated the retention of the avoidance response (FIG. 2).

B. Mouse Elevated Plus-Maze Studies

The mouse elevated plus-maze is a conflict test that probes anxiolytic activity of test compounds (Lister, Psychopharmacology, 1987, 92:180). It is based on the fact that exposure of mice to an elevated open arm leads to an avoidance response considerably stronger than that evoked by exposure to an enclosed arm.

The apparatus required to perform this test is made of plywood and consists of two open arms (17×8 cm) and two enclosed arms (17×8×15 cm) extending from a central platform (8×8 cm). It is mounted on a plywood base rising 39 cm above the floor. Mice are released on the central platform and the time spent in the open and enclosed arms is recorded during a 5 minute test period. (−)Nicotine (0.1 and 0.3 mmol/kg, p<0.05) induced a significant increase in the time spent by the mice in the open arms of the maze (a measure of anxiolytic effect) as compared to saline-injected mice.

Figure 4:
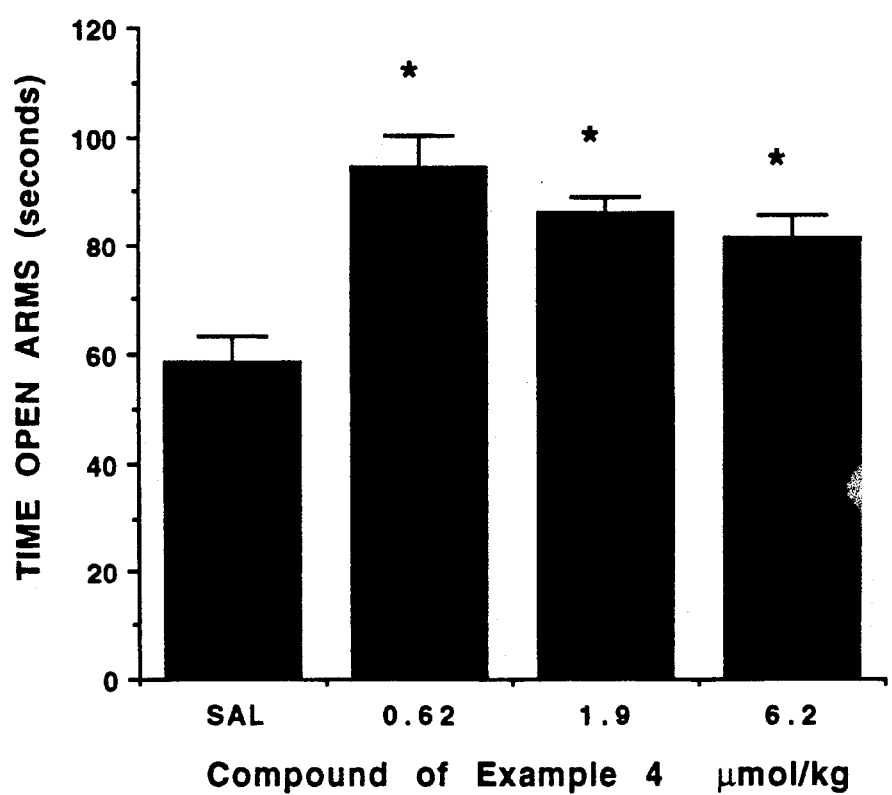
FIG. 4 is a graphical representation of the effects of the compound of Example 4 (0.003-0.3 mg/kg) on the performance of CD1 mice in the Elevated-Plus Maze Study expressed as median time (seconds) spent on the open arms of the maze.

FIG. 4 demonstrates that the compound of Example 4 has an anxiolytic effect similar to (−)nicotine. The compound of Example 4 (0.62-6.2 μmol/kg, IP) was administered to CD1 mice 15 minutes before the test. There was a clear anxiolytic response in mice receiving 0.62-6.2 μmol/kg of the compound of Example 4 (p<0.05) as these groups of mice spent significantly more time in the open arms of the maze as compared to control animals.

TABLE 1

Binding to Neuronal Nicotinic Receptors

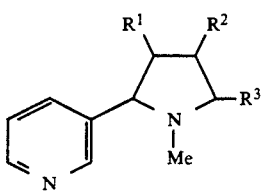

| Exam. No. | $R^1$ | $R^2$ | $R^3$ | Ki (nM) | n* |
|---|---|---|---|---|---|
| nicotine | H | H | H | 1.0 | 4 |
| 1 | H | —OH | H | 29 | 2 |
| 2 | H | —OCH$_3$ | H | 25 | 2 |

TABLE 1-continued

Binding to Neuronal Nicotinic Receptors

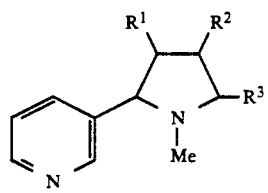

| Exam. No. | $R^1$ | $R^2$ | $R^3$ | Ki (nM) | n* |
|---|---|---|---|---|---|
| 3 | H | —F | H | 35 | 2 |
| 4 | H | —CH$_3$ | H | 4.2 | 2 |
| 5 | H | —CH$_2$F | H | 135 | 2 |
| 6 | H | —CH$_2$CH$_3$ | H | 53 | 2 |
| 7 | H | —CH$_2$OH | H | 318 | 2 |
| 7 | H | —CH$_2$OH | H | 139 | 2 |
| 8 | H | —CH$_2$F | H | 10 | 2 |
| 9 | CH$_2$F | H | H | 106 | 3 |
| 10 | CH$_3$ | H | H | 23 | 2 |
| 11 | H | —CN | H | 7 | 2 |
| 12 | H | —OCOCH$_3$ | H | 162 | 2 |
| 13 | CH$_3$ | CH$_3$ | H | 105 | 2 |
| 14 | H | H | —Me | 1066 | 3 |
| 14 | H | H | —Me | 36 | 3 |
| 15 | H | H | —Bu | 1590 | 3 |
| 15 | H | H | —Bu | 127 | 3 |
| 16 | H | —CH$_2$CN | H | 53 | 3 |
| 19 | H | OMs | H | 276 | 1 |

*Number of determinations

The present invention includes one or more of the compounds of formula (I) formulated into compositions together with one or more non-toxic pharmaceutically-acceptable carriers, adjuvants or vehicles, which are collectively referred to herein as carriers, for parenteral injection, for oral administration in solid or liquid form, for rectal administration, and the like.

In order to reduce unwanted peripherally mediated side-effects, it is advantageous, but not essential, to incorporate into the composition a peripherally acting anti-cholinergic such as N-methylscopolamine, N-methylatropine, propantheline, methantheline, or glycopyrrolate.

Compositions suitable for parenteral injection may comprise pharmaceutically-acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration may include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills and granules may be prepared with coatings and shells, such as enteric coatings and others well known in this art. They may contain opacifying agents, and may also be of such composition that they release the active compound or compounds in a certain part of the intestinal tract in a delayed manner. Examples of embedding compositions which may be used are polymeric substances and waxes.

The active compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, these liquid dosage forms may also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or vaginal administrations are preferably suppositories which can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a compound of this invention include powders, sprays and inhalants. The active component is admixed under sterile conditions with a pharmaceutically-acceptable carrier and any needed preservative, buffers or propellants as may be required. Ophthalmic formulations, eye ointments, powders and solutions are also contemplated as being within the scope of this invention.

The present compounds can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically-acceptable and metabolizable lipid capable of forming liposomes can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p 33 et seq.

Actual dosage levels of active ingredient in the compositions of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of the compounds of this invention administered to a host in single or divided doses may be in amounts as determined by the attending physician, typically, for example, of from about 0.001 to 100 mg/kg body weight daily and preferably 0.01 to 10 mg/kg/day. Dosage unit compositions may contain such amounts of submultiples thereof to make up the daily dose. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidentally with the specific compound employed; and like factors well known in the medical arts.

The following examples, which are provided for illustration and not limitation of the invention, will serve to further illustrate preparation of the novel compounds of the invention and their biological activity.

Thin-layer chromatography (TLC) was performed on 0.25 mm E. Merck precoated silica gel plates (60 F-254). Flash chromatography was performed on 200-400 mesh silica gel (E. Merck), while column chromatography was performed on 70-230 mesh silica gel (E. Merck).

The following abbreviations are used: THF for tetrahydrofuran, DMF for N,N-dimethylformamide, $D_2O$ for deuterium oxide, $CDCl_3$ for deuterochloroform, DMSO-$d_6$ for deuterodimethylsulfoxide, BOC for t-butyloxycarbonyl, CBZ for benzyloxycarbonyl, Bz for benzyl, Ms for methanesulfonyl, PAW for pyridine/acetic acid/water (20:6:11), DCC for dicyclohexylcarbodiimide, DIBAL for diisobutylaluminum hydride, DIEA for diisopropylethylamine, DPPA for diphenylphosphoroazidate, EDCl for 1-(3-dimethyl-aminopropyl)-3-ethylcarbodiimide hydrochloride, EtOH for ethanol, IBCF for isobutyl chloroformate, HOAc for acetic acid, HOBT for 1-hydroxybenzotriazole, LAH for lithium aluminum hydride, $NH_4OAc$ for ammonium acetate, NMM for N-methylmorpholine, TEA for triethylamine.

EXAMPLE 1

4'-(R)-Hydroxynicotine oxalate 1a. 3-(R)-Hydroxycotinine

A sample of cotinine (1.2 g, 6.8 mmol, from Aldrich Chemical Co.) was dissolved in 30 mL of THF and cooled to −78° C. Lithium diisopropyl amide (LDA) solution (1.5M in hexane, 13.6 mmol) was added and the solution was stirred and warmed to 0° C. for 30 min. The solution was cooled to −78° C. and 2.5 g (10.9 mmol) of (+)-(camphorylsulfonyl)oxaziridine dissolved in 24 mL of THF was added. The reaction was stirred for 2 hours and quenched by addition of methanol. This mixture was stirred for 15 min, and the solvent was removed. The residue was subjected to flash chromatography on silica gel using chloroform:methanol (100:7) as eluent. The title compound was isolated as an oil (1.1 g, 84% yield). MS M/Z: 193 (M+H)+. $^1H$ NMR ($CDCl_3$, 300 MHz)d: 2.34 (ddd, J=13.5, 9.0, 3.0 Hz, 1H), 2.51 (m, 1H),.2.78 (s, 3H), 4.57 (t, J=7.5 Hz, 1H), 4.66 (dd, J=9.0, 3.0 Hz, 1H), 7.45 (m, 1H), 7.35 (dd, J=9.0, 6.0 Hz), 8.61 (dd, J=5.6, 3 Hz, 1H), 8.49 (d, J=3 Hz, 1H).

1b. 4'-(R)-Hydroxynicotine

To the product of Example 1a (357 mg, 1.86 mmol) in 2 mL of THF was added under nitrogen and dropwise over a period of 5 minutes 3.71 mL (3.71 mmol) of a 1M solution of borane in THF. After stirring under reflux for 2 hours, methanol was added dropwise and the reaction stirred for an additional 15 minutes. The solvent was then removed in vacuo, affording a white solid borane complex. This solid was dissolved in anhydrous ethanol. Cesium fluoride (1.30 g, 11.16 mmol) was added, and the resultant solution was stirred under reflux overnight. Evaporation of the solvent provided a white solid which was purified on a silica gel column, eluting with chloroform:methanol (10:1) to give 105 mg of the desired alcohol as an oil in 32% yield. MS M/Z: 179 (M+H)+. $^1H$ NMR ($CDCl_3$) δ: 2.03-2.10 (m, 2H), 2.18 (s, 3H), 2.33 (dd, J=5.2, 10 Hz, 1H), 3.52 (dd, J=7.3, 9.5 Hz), 3.59 (dd, J=6.7, 10.3 Hz, 1H), 4.47 (,m, 1H), 7.43 (dd, J=5.2, 7.7 Hz, 1H), 7.85 (dt, J=5.9, 1.8 Hz, 1H), 8.45 (dd, J=5.2, 1.5 Hz, 1H), 8.50 (d, J=1.5 Hz, 1H).

1c. 4'-(R)-Hydroxynicotine oxalate

A solution of the product 1b (34 mg, 0.19 mmol) in ethanol was added dropwise to a stirred solution of oxalic acid (25 mg, 0.28 mmol) in diethyl ether at room temperature. The resultant white precipitate was then collected by centrifugation and triturated with three portions of diethyl ether. The hygroscopic solid was obtained in 50% yield (25.4 mg). mp 208°-210° C. MS M/Z (DCl/NH3): 179 (M+H)+, 196 (M+NH4+). $^1H$ NMR ($D_2O$) δ: 2.55 (dd, J=6, 13 Hz), 2.73 (m, 2H), 2.96 (s, 3H), 3.37 (m, 1H), 4.19 (m, 1H), 4.93 (m, 1H), 7.82 (m, 1H), 8.32 (d, J=9 Hz, 1H), 8.71 (d, J=6 Hz), 8.82 (s, 1H),. Anal. calcd for $C_{12}H_{16}N_2O_5 \bullet H_2O$: C, 50.35; H, 6.34; N, 9.79. Found: C, 49.99; H, 6.54; N, 9.70.

EXAMPLE 2

4'-(R)-Methoxynicotine oxalate 2a. 3-(R)-Methoxycotinine

A 80 mg (2 mmol) sample of 3-(R)-hydroxycotinine, from Example 1b, was dissolved in THF containing sodium hydride and stirred at room temperature for 15 minutes. Tetrabutylammonium iodide (20 mg, 0.05 mmol) and methyl iodide (0.020 mL, 0.32 mmol) were then added to the reaction mixture. After stirring at room temperature for 20 hours, the solvent was evaporated under reduced pressure. The crude product was purified on flash silica column. Elution with chloroform/methanol (20:1) gave 17 mg (53%) of title compound. MS M/Z (DCl/NH3): 207 (M+H)+, 224 (M+NH4)+. $^1H$ NMR ($CDCl_3$) δ: 2.14-2.26 (m, 1H), 2.42-2.55 (m, 1H), 2.73 (s, 3H), 3.32-3.43 (m, 3H), 3.58 (s, 3H), 4.12 (m, 1H), 4.66 (m, 1H), 7.36 (m, 1H), 7.47 (m, 1H), 8.5 (m, 1H), 8.62 (m, 1H).

2b. 4'-(R)-Methoxynicotine

The product of Example 2a (170 mg, 0.83 mmol) was treated with borane followed by cesium fluoride as described in Example 1b. The crude product was purified by flash chromatography on silica gel eluting with acetone/hexane (1:1) to give 36 mg (23% yield for 2 steps). MS M/Z (DCl/NH3): 191 (M+H)+, 208 (H+NH4)+. $^1H$ NMR ($D_2O$) δ: 1.4-1.52 (m, 1H), 1.88-197 (m, 2H), 2.09-2.12 (m, 1H), 2.15 (s, 3H), 2.6-2.7 (m, 1H), 3.13-3.41 (m, 2H), 3.37 (s, 3H), 7.25-7.29 (m, 1H), 7.70 (d, J=7.7 Hz, 1H), 8.51 (dd, J=4.8, 1.5, 1H), 8.53 (d, J=1.5 Hz, 1H).

2c. 4'-(R)-Methoxynicotine oxalate

By the procedure as described in Example 1c, the product of Example 2b was converted to the oxalate salt in quantitative yield to give 64 mg of the title compound as a very hygroscopic salt. MS M/Z (DCl/NH3): 193 (M+H)+, 210 (M+NH4)+. $^1H$ NMR ($D_2O$) δ: 2.60-2.70 (m, 1H), 2.74-2.81 (m, 1H), 2.92 (s, 3H), 3.42 (s, 3H), 3.46-3.55 (m, 1H), 4.25 (m, 1H), 4.88 (m, 1H), 4.44 (m, 1H), 8.09 (dd, J=5, 8.1 Hz, 1H), 8.67 (d, J=8.1 Hz, 1H), 8.89 (d, J=5.6 Hz, 1H), 8.99 (s, 1H). Anal. calcd. for $C_{11}H_{16}N_2O \bullet 2.8\ C_2H_2O_4 \bullet H_2O$: C, 46.33; H, 5.53; N, 6.51. Found: C, 46.40; H, 5.20; N, 6.89.

EXAMPLE 3

4'-(S)-Fluoronicotine dioxalate 3a. 4'-(R)-Methanesulfonyloxynicotine

Under a nitrogen atmosphere, in a 50 mL round-bottom flask equipped with a rubber septum and a magnetic stir bar were placed 554 mg (2.89 mmol) of 4'-(R)-hydroxynicotine (from Example 1b) and 20 mL of dichloromethane. To this stirring solution, at room temperature, was added 0.59 mL (4.62 mmol) of triethylamine followed by 0.34 mL of methanesulfonyl chloride (4.34 mmol). The reaction mixture was stirred for 19 hours, when it was quenched with methanol to destroy excess methanesulfonyl chloride. The reaction mixture was concentrated with a rotary evaporator to obtain a dark yellow oil. This crude material was subjected to flash column chromatography on silica gel, gradually increasing the polarity of the eluent from 20:1 chloroform/methanol to 100:7 chloroform/methanol to obtain 420 mg (57% yield) of the title compound as pale yellow viscous oil. MS M/Z (DCl/NH3): 257 (M+H)+, 264 (M+NH4)+. 1H NMR (CD3OD) δ: 2.24 (s, 3H),2.65-2.61 (m, 2H), 3.07 (s, 3H), 3.65-3.74 (m, 1H), 3.75-3.85 (m, 1H), 4.25-4.32 (m, 2H), 5.24-5.34 (m, 1H), 7.62 (dd, J=6, 7.5 Hz, 1H), 8.09 (d, J=7.5 Hz, 1H), 8.51 (d, J=6 Hz, 1H), 8.59 (s, 1H).

3b. 4'-(S)-Fluoronicotine oxalate

The product from Example 3a (21 mg, 0.08 mmol) was placed in a 10 mL roundbottomed flask and 0.5 mL of 1M tetra-n-butylammonium fluoride in THF was added to the system. This solution was heated under reflux under nitrogen for overnight. The reaction mixture was concentrated with a rotary evaporator, and the residue was taken up with in chloroform. The crude material was purified by flash column chromatography on silica gel, eluting with hexane/acetone (1:1) to provide 10.5 mg (70% yield) of the title compound as yellow oil. The oil was dissolved in diethyl ether to which was added, dropwise, a solution of oxalic acid (11 mg, 0.11 mmol) in diethyl ether. The resultant precipitate was collected by centrifugation to give 13 mg of the title compound. MS M/Z (DCl/NH3): 181 (M+H)+, 198 (M+NH4)+. 1H NMR (D2O) δ: 2.60-2.78 (m, 1H). 2.91 (s, 3H), 3.16-3.34 (m, 1H), 3.52-3.72 (m, 1H), 4.06-4.16 (m, 1H), 4.77 (dd, J=7.3, 10.3 Hz, 1H), 5.65 (br d, J=36.7 Hz, 1H), 7.87 (dd, J=8.1, 5.1 Hz, 1H), 8.40 (d, J=8.1 Hz, 1H), 8.79 (d, J=5.5 Hz, 1H), 8.85 (d, J=2.2 Hz, 1H), Anal. calcd. for $C_{10}H_{13}N_2F \cdot 2.2 C_2H_2O_4$: C, 45.72; H, 4.64; N, 7.40. Found: C, 45.92; H, 4.92; N, 6.93.

EXAMPLE 4

4'-(R)-Methylnicotine dioxalate 4a. 3-(R)-Methylcotinine

A solution of 1.5M solution of lithium diisopropyl amide solution (3.40 mL, 5.11 mmol) in tetrahydrofuran was added dropwise to a solution of cotinine (819 mg, 4.65 mmol) in 30 mL of tetrahydrofuran at −78° C. After stirring at −78° C. for 15 minutes, the reaction temperature was raised to 0° C., and the resultant solution was allowed to stirred for an additional 30 minutes. The solution was cooled to −78° C., then methyl iodide (0.304 mL, 4.88 mmol) was added dropwise. After 2 hours at −78° C. to −20° C., the reaction was quenched at 0° C. with methanol. The organic solvent was concentrated in vacuo to give yellow oil. The oil was purified by flash column chromatography on silica gel eluting with acetone/hexane (3:1) to give 683 mg (77%) of the title compound as a colorless oil. MS M/Z (CDl/NH3): 190 (M+H)+, 208 (M+NH4)+. 1H NMR (CDCl3) δ: 1.27 (d, J=7.5 Hz, 3H).2.12-2.20 (m, 2H), 2.63-2.74 (m, 1H), 2.74 (s, 3H), 4.54 (dd, J=4.5,8.0 Hz, 1H), 7.33 (ddd, J=1.0, 4.5, 8.0 Hz, 1H), 7.48 (dt, J=2.5, 8.0 Hz, 1H), 8.49 (d, J=2.5 Hz, 1H), 8.59 (dd, J=2.0, 4.5 Hz, 1H), 4b. 4'-(R)-Methylnicotine The product of Example 4a was treated dropwise with 1M solution of borane in tetrahydrofuran. After the reaction was complete, the crude reaction product was treated with cesium fluoride as described in Example 1b. The crude product was purified by flash column chromatography on silica gel eluting with acetone/hexane (1:1) to give the title compound as a colorless oil. MS M/Z (DCl/NH3): 177 (M+H)+, 191 (M+NH4+). 1H NMR(CDCl3) δ: 1.07 (d, J=7.0 Hz, 3H), 1.78-1.83 (m, 1H), 1.93-2.0 (m, 2H), 2.16 (s, 3H), 2.42-2.50 (m, 1H), 3.21 (t, J=8.1 Hz, 1H), 3.36 (dd, J=7, 9.2 Hz, 1H), 7.26 (dd, J=4.5, 8 Hz, 1H), 7.70 (dt, J=2, 8 Hz, 1H), 8.49 (dd, J=2, 4.5 Hz, 1H), 8.52 (d, J=2 Hz, 1H).

4c. 4'-(R)-Methylnicotine dioxalate

To the solution of the product from Example 4b in 1.5 mL of diethyl ether was added oxalic acid in diethyl ether dropwise at 0° C. The solution was stirred at 0° C. for 15 minutes, and the precipitate was collected by centrifugation, washed with diethyl ether three times and dried in vacuo to yield the title compound as a white powder. MS M/Z (DCl/NH3): 177 (M+H)+, 194 (M+NH4)+. 1H NMR (D2O) δ: 1.23 (d, J=6.6 Hz, 3H), 2.28-2.42 (m, 1H), 2.54-2.68 (m, 1H), 2.80 (m, 1H, overlap with 2.84 peak), 2.84 (s, 3H), 3.04 (m, 1H), 4.72 (brs, 1H), 3.98 (m, 1H), 7.98 (dd, J=5.5, 8.0 Hz, 1H), 8.49 (d, J=8.1 Hz, 1 Hz), 8.83 (d, J=5.5 Hz, 1H), 8.89 (s, 1H),. Anal. calcd. for $C_{11}H_{16}N_2 \cdot 2.4 C_2H_2O_4 \cdot H_2O$: C, 51.75; H, 6.54; N, 8.75. Found: C, 52.05; H, 6.86; N, 8.64.

EXAMPLE 5

4'-(S)-Benzylnicotine dioxalate 5a. 3-(S)-Benzylcotinine

A 1.5M solution of lithium dissopropyl amide solution (1.48 mL, 2.22 mmol) in tetrahydrofuran to was added dropwise to cotinine (300 mg, 1.70 mmol) in 15 mL of tetrahydrofuran at −78° C. After stirring at −78° C. for 15 min, the reaction temperature was raised to 0° C. and the resultant solution allowed to stirred for an additional 30 minutes. The enolate solution was cooled to −78° C. followed by dropwise addition of benzyl bromide (0.303 mL, 2.25 mmol). After 2 hours at −78° C. to −20° C., the reaction was quenched at 0° C. with methanol. The organic solvent was concentrated in vacuo to give a yellow oil. The oil was purified by flash column chromatography on silica gel eluting with chloroform/methanol (20:1) to give 410 mg (90%) of the title compound as a colorless oil. MS M/Z (CDl/NH3): 267 (M+H)+, 284 (M+NH4)+. 1H NMR (CDCl3) δ: 1.88-1.98 (m, 1H), 2.25-2.37 (m, 1H), 2.74 (s, 3H), 2.81 (dd, J=8.0, 13.5 Hz, 1H), 2.90-3.01 (m, 1H), 3.22 (dd, J=4.0, 13.5 Hz, 1H), 4.21 (dd, J=4.0, 8.0 Hz, 1H), 7.16-7.43 (m, 1H), 7.52 (d, J=8.0 Hz, 1H), 8.41 (m, 1H), 8.57 (d, J=4.5 Hz, 1H).

5b. 4'-(S)-Benzylnicotine

The product of Example 5a (410 mg, 1.54 mmol) in tetrahydrofuran was treated dropwise with 1M solution of borane (4.62 mL, 4.62 mmol) in tetrahydrofuran at room temperature. After reflux for 3 hours, the reaction was quenched by addition of a large excess of methanol. The resultant solution was allowed to stir at room temperature for an additional 15 min. Solvent was then removed under reduced pressure to give a white solid. The crude reaction product was dissolved in ethanol and treated with cesium fluoride (535 mg, 4.62 mmol) as described in Example 1b. The crude product was purified by flash column chromatography on silica gel, eluting with chloroform/methanol (10:1) to give 120 mg of the title compound (31% for 2 steps) as a colorless oil. MS M/Z (DCl/NH3): 253 (M+H)+. 1H NMR (CDCl$_3$) δ: 8.53 (d, J=2.2 Hz, 1H), 8.50 (d, J=4.4 Hz, 1H), 7.6–7.7 (m, 1H), 7.10–7.31 (m, 6H), 3,16–3.45 (m, 2H), 2.73 (s, 3H), 2.19–2.33 (m, 4H), 1.92–2.19 (m, 2H).

5c. 4'-(S)-Benzylnicotine dioxalate

To the solution of the product from Example 5b in 1.5 mL of diethyl ether was added oxalic acid in diethyl ether dropwise at 0° C. After stirring at 0° C. for 15 minutes, the precipitate was collected by centrifugation, washed with diethyl ether (3×) and dried in vacuo to yield the title compound as a white powder. MS M/Z (DCl/NH3): 253 (M+H)+, 270 (M+NH$_4$)+. 1H NMR (D$_2$O) δ: 2.50–2.52 (m, 2H), 2.82 (s, 3H), 2.94 (d, J=8.1 Hz, 1H), 3.01–3.24 (m, 1H), 3.14–3.27 (m, 1H), 3.82–3.96 (m, 1H), 4.6–4.83 (m, 1H, overlap with D$_2$O peak), 7.32–7.42 (m, 5H), 7.93 (dd, J=5.5, 8.4 Hz, 1H), 8.43 (m, 1H), 8.79 (dd, J=1.5, 5.6 Hz, 1H), 8.84 (d, J=2.9 Hz, 1H). Anal. calcd. for C$_{17}$H$_{20}$N$_2$•C$_2$H$_2$O$_4$: C, 59.56; H, 5.97; N, 6.90. Found: C, 59.78; H, 5.74; N, 6.90.

EXAMPLE 6

4'-(S)-Ethylnicotine dioxalate 6a. 3-(S)-Ethylcotinine

The enolate solution was generated by dropwise addition of 1.5M solution of lithium diisopropyl amide solution (1.36 mL, 2.0 mmol) in tetrahydrofuran to cotinine (300 mg, 1.70 mmol) in 15 mL of tetrahydrofuran at −78° C. After stirring at −78° C. for 15 minutes, the reaction temperature was raised to 0° C., and the resultant solution allowed to stirred for an additional 30 minutes. The solution was cooled to −78° C. followed by dropwise addition of ethyl iodide (0.204 mL, 2.55 mmol). After 2 hours at −78° C. to −20° C., the reaction was quenched at 0° C. with methanol. The organic solvent was concentrated in vacuo to give dark yellow oil. The oil was purified by flash column chromatography on silica gel eluting with acetone/hexane (1:1) to give 240 mg (69% yield) of the title compound as a colorless oil. MS M/Z (CDl/NH3): 205 (M+H)+, 222 (M+NH$_4$)+. 1H NMR (CDCl$_3$) δ: 0.98 (t, J=7.5 Hz, 3H), 1.50 (m, 1H), 1.94 (m, 1H), 2.23 (m, 1H), 2.58 (m, 1H), 2.73 (s, 3H), 4.54 (dd, J=3, 9 Hz, 1H), 7.35 (m, 1H), 7.50 (m, 1H), 8.49 (brs, 1H), 8.60 (brs, 1H).

6b. 4'-(S)-Ethylnicotine

The product of Example 6a (240 mg, 1.26 mmol) in 6 mL of tetrahydrofuran was treated dropwise with 1M solution of borane (3.79 mL, 3.79 mmol) in tetrahydrofuran at room temperature. After reflux for 3 hours, the reaction was quenched by addition of a large excess of methanol. The resultant solution was allowed to stir at room temperature for an additional 15 minutes. Solvent was then removed under reduced pressure to give a white solid. The crude reaction product was dissolved in 12 mL of dioxane and treated with cesium fluoride (292 mg, 2.52 mmol) as described in Example 1b. The crude product was purified by flash column chromatography on silica gel eluting with acetone/hexane (1:1) to give 136 mg of the title compound (56% yield for 2 steps) as a colorless oil. MS M/Z (DCl/NH3): 191 (M+H)+, 208 (M+NH$_4$)+. 1H NMR (CDCl$_3$) δ:0.92 (t, J=7.5 Hz, 3H), 1.36 (dd, J=7.5, 13.5 Hz, 1H), 1.44 (dd, J=7.5, 13.5 Hz, 1H), 1.78–1.93 (m, 1H), 1.93–2.06 (m, 1H), 2.16 (s, 3H), 2.16–2.37 (m, 1H), 3.26 (m, 1H), 3.37 (m, 1H), 7.25 (m, 1H, overlap with CHCl$_3$), 7.71 (m, 1H), 8.49 (dd, J=3.0, 6.0 Hz, 1H), 8.52 (d, J=3 Hz, 1H).

6c. 4'-(S)-Ethylnicotine dioxalate

To the solution of the product from Example 6b in 1.5 mL of diethyl ether was added oxalic acid in 5 mL of diethyl ether dropwise at 0° C. After stirring at 0° C. for 15 min, the precipitate was collected by centrifugation, washed with diethyl ether three times and dried in vacuo to yield the title compound as a white powder. MS M/Z (DCl/NH3): 177 (M+H)+, 194 (M+NH$_4$)+. 1H NMR (D$_2$O) δ:0.97 (t, J=7.5 Hz, 3H), 1.61 (m, 2H), 2.31–2.46 (m, 1H), 2.50–2.70 (m, 2H), 2.82 (s, 3H), 3.04–3.14 (m, 1H), 3.90–4.04 (m, 1H), 4.60–4.70 (m, 1H, overlap with D2O peak), 7.79 (dd, J=4.5, 8.0 Hz, 1H), 8.29 (d, J=9.0, 1.5 Hz, 1H), 8.74 (d, J=6.08. Hz, 1H), 8.78 (d, J=1.5 Hz, 1H). Anal. calcd. for C$_{12}$H$_{18}$N$_2$•C$_2$H$_2$O$_4$: C, 50.72; H, 5.81; N,7.21. Found: C, 51.11; H, 5.81, N, 7.21.

EXAMPLE 7

4'(R)-Hydroxymethylnicotine dioxalate 7a. 3-(S)- and 3-(R)-Hydroxymethylcotinine The enolate solution was generated by dropwise addition of 1.5M solution of lithium diisopropyl amide solution (1.67 mL, 2.5 mmol) in tetrahydrofuran to cotinine (352 mg, 2.00 mmol) in 18 mL of tetrahydrofuran at −78° C. After stirring at −78° C. for 15 minutes, the reaction temperature was raised to 0° C. and the resultant solution allowed to stirred for an additional 30 min. The enolate solution was cooled to −78° C. followed by passage of anhydrous gaseous formaldehyde in a stream of nitrogen (the formaldehyde was generated by the thermal depolymerization of paraformaldehyde at 160° C.). After 2 hours at −78° C. to −20° C., the reaction was quenched at 0° C. with methanol. The organic solvent was concentrated in vacuo to give dark yellow oil. The oil was purified by flash column chromatography on silica gel eluting with chloroform/methanol (100:7) to give 242 mg (59% yield) of the title compound as a colorless oil. MS (CDl/NH$_3$) M/Z:207 (M+H)+, 224 (M+NH$_4$)+. 1H NMR (CDCl$_3$) δ:1.68–1.80 (m, 1H, overlap with water peak), 2.05 (ddd, J=3.0, 6.0, 9.0 Hz, 1H), 2.23 (m, 1H), 2.41 (dt, J=12, 9 Hz, 1H), 2.65 (s, 1H), 2.76 (s, 2H), 3.72–3.83 (m, 1H), 3.93–4.05 (m, 1H), 4.52 (t, J=7.5 Hz, 1/3H), 4.60 (dd, J=9, 3.0 Hz, 2/3H), 7.47–7.53 (m, 2/3H), 7.59–7.64 (m, 1/3H), 8.47–8.66 (m, 1H), 8.57–8.66 (m, 1H).

7b. 4'-(S)- and 4'-(R)-Hydroxymethylnicotine

The product of Example 7a (735 mg, 3.57 mmol) in 10 mL of tetrahydrofuran was treated dropwise with 1M solution of borane (10.7 mL, 10.7 mmol) in tetrahydrofuran at room temperature. After reflux for 3 hours, the reaction was quenched by addition of a large excess of methanol. The resultant solution was allowed to stir at room temperature for an additional 15 min. Solvent was then removed under reduced pressure to give a white solid. One fifth of this crude reaction product (160 mg, 0.83 mmol) was dissolved in 8 mL of dioxane and treated with cesium fluoride (290 mg, 2.50 mmol) as described in Example 1b. The crude product was purified by flash column chromatography on silica gel eluting with chloroform/methanol (10:1) to give, in order of elution, 23 mg of 4'(R)-hydroxymethylnicotine (14% yield for 2 steps) and 69 mg of 4'-(S)-hydroxymethylnicotine (14% yield for 2 steps) as a colorless oil. The 4'-R isomer exhibits the following spectral characteristics: MS M/Z (DCI/NH3): 193 (M+H)+. 1H NMR (CDCl$_3$) δ:1.65–1.78 (m, 1H), 2.18 (s, 3H), 2.51–2.63 (m, 1H), 3.13–3.30 (m, 2H), 3.66 (dd, J=4.5, 9.0 Hz, 1H), 3.79 (dd, J=4.5, 9.0 Hz, 1H), 7.29 (m, 1H, overlap with CDCl$_3$), 7.83 (d, J=7.5 Hz, 1H), 8.53 (m, 2H). Anal. calcd. for C$_{11}$H$_{16}$N$_2$O•0.05 CHCl3: C, 66.95; H, 7.96;

N, 14.21. Found: C, 66.87; H, 7.92, N, 14.11. 4'-(S)-isomer: MS M/Z (DCl/NH3): 193 (M+H)+. $^1$H NMR (CDCl3) δ:1.88–2.10 (m, 2H), 2.19 (s, 3H), 2.54–2.72 (m, 1H), 3.24 (t, J=7.5 Hz, 1H), 3.45 (t, J=8.0 Hz, 1H), 3.66 (m, 2H), 7.28 (m, 1H, overlap with CDCl3), 7.76 (d, J=7.5 Hz, 1H), 8.52 (dd, J=3.0, 4.5 Hz, 1H), 8.54 (d, J=3.0 Hz, 1H). Anal. calcd. for $C_{11}H_{16}N_2O$•0.05 CHCl3: C, 66.95; H, 7.96; N, 14.21. Found: C, 67.10; H, 7.96, N, 14.21.

EXAMPLE 8

4-(R)-Fluoromethylnicotine oxalate 8a. 4'-(R)-Methanesulfonyloxymethylnicotine A 410 mg (2.0 mmol) sample of 3-hydroxymethylcotinine (the product of Example 7a) in 10 mL of tetrahydrofuran was treated dropwise with 1M solution of borane (6.0 mL, 6.0 mmol) in tetrahydrofuran at room temperature. After reflux for 3 hours, the reaction was quenched by addition of a large excess of methanol. The resultant solution was allowed to stir at room temperature for an additional 15 minutes. Solvent was then removed under reduced pressure to give a white solid. This solid was used for next reaction without further purification. Thus, under a nitrogen atmosphere, in a 50 mL round-bottom flask equipped with a rubber septum and a magnetic stir bar were placed product from previous reaction 440 mg (2.0 mmol) and 25 mL of dichloromethane. To this stirring solution, at room temperature, was added 0.34 mL (8.0 mmol) of pyridine followed by 0.42 mL of methanesulfonyl chloride (3.0 mmol). The reaction mixture was stirred for 19 hours. It was then quenched with methanol to destroy excess methanesulfonyl chloride. The reaction mixture was concentrated with a rotary evaporator to obtain a dark yellow oil. This crude material was subjected to flash column chromatography on silica gel, gradually increasing the polarity of the eluent from 2:1 hexane/acetone to 1:1 hexane/acetone to obtain 350 mg (65% yield) of the BH3 complex of the methanesulfonate ester (2:1 mixtures of 2 isomers) as pale yellow viscous oil. MS M/Z (DCl/NH3): 271 (M+H)+, 300 (M+NH3+BH3)+. $^1$H NMR (CDCl3) δ:1.88–1.95 (m, 1H), 2.10–2.20 (m, 1H), 2.32 (s, 1H), 2.50 (s, 2H), 2.78–2.96 (m, 2H), 3.04 (s, 1H), 3.09 (s, 2H), 3.30–3.48 (m, 1H), 3.70–3.88 (m, 1H), 4.25–4.34 (m, 2H), 7.53–7.62 (m, 1H), 8.24 (d, J=9.0 Hz, 1/3H), 8.40 (d, J=9 Hz, 2/3H), 8.50–8.72 (m, 2H).

8b. 4'-(R)-Fluoromethylnicotine

The product from Example 8a (104 mg, 0.39 mmol) was placed in a 10 mL round-bottomed flask and 2.31 mL of 1M tetra-n-butylammonium fluoride in THF was added to the system. This solution was heated under reflux under nitrogen for 3 hours. The reaction mixture was concentrated with a rotary evaporator, and the residue was taken up with in chloroform. The crude material was purified by flash column chromatography (50 g of silica gel), eluting with hexane/acetone (1:2) to provide 12 mg (16% yield) of the title compound as yellow oil. MS M/Z (DCl/NH3): 195 (M+H)+, 212 (M+NH4)+. $^1$H NMR (CDCl3) δ:1.92–2.17 (m, 2H), 2.23 (s, 3H), 2.60–2.92 (m, 1H), 3.11–3.47 (m, 1H), 3.40–3.60 (m, 1H), 4.43 (dd, J=6.0, 48 Hz, 2H), 7.25 (m, 1H, overlap with CDCl3 peak), 7.65–7.90 (m, 1H), 8.55 (m, 2H).

8c. 4'-(R)-Fluoromethylnicotine oxalate

To the solution of the product from Example 8b in 1.5 mL of diethyl ether was added oxalic acid in 5 mL of diethyl ether dropwise at 0° C. After stirring at 0° C. for 15 minutes, the precipitate was collected by centrifugation, washed with diethyl ether three times and dried in vacuo to yield the title compound as a white powder. MS M/Z (DCl/NH3): 195 (M+H)+, 212 (M+NH4)+. $^1$H NMR (D2O) δ:2.52–2.76 (m, 2H), 2.84 (s, 3H), 3.0–3.23 (m, 1H), 3.30–3.43 (m, 1H), 4.01–4.13 (m, 1H), 4.64 (dd, J=56.0, 48 Hz, 2H), 4.67–4.80 (m, 1H, overlap with D2O peak), 7.91 (dd, J=7.5, 4.5 Hz, 1H), 8.45 (d, J=9.0, 1H), 8.81 (d, J=6.1 Hz, 1H), 8.87 (s, 1H). Anal. calcd. for $C_{11}H_{15}N_2F$•2.1 $C_2H_2O_4$•0.5 Et2O: C, 49.13; H, 5.80; N, 6.66. Found: C, 48.80; H, 6.12, N, 6.29.

EXAMPLE 9

3'-Fluoromethylnicotine oxalate 9a. 4-Hydroxymethylcotinine

A 557 mg (2.38 mmol) sample of methyl trans-4-cotininecarboxylate (prepared from the acid, which is available from Aldrich Chemical Co.) in 20 mL of methanol was cooled to 0° C. Sodium borohydride (135 mg, 3.57 mmol) was added portionwise to the reaction mixture under nitrogen at 0° C. After stirring 10 minutes at 0° C., the reaction was warmed to room temperature and allowed to stir for an additional 2 hours. After the reaction was completed, it was quenched by addition of saturated aqueous sodium bicarbonate solution. The desired product was extracted into chloroform from water by a continuous extraction method. The solvent was removed under reduced pressure to give a light yellow oil which was chromatographed on silica gel. Elution with chloroform/methanol (10:1) provided the title compound (477 mg, 97% yield) as a colorless oil. MS M/Z (DCl/NH3): 207 (M+H)+, 224 (M+NH4)+. $^1$H NMR (CDCl3) δ:2.30–2.41 (m, 2H), 2.49 (s, 3H), 2.65–2.77 (m, 1H), 3.70–3.76 (m, 2H), 4.49 (d, J=6 Hz, 1H), 7.35 (dd, J=4.5, 9.0 Hz), 7.55 (dt, J=2.5, 9.0 Hz, 1H), 8.53 (d, J=2.5 Hz, 1H), 8.61 (dd, J=2.5, 4.5 Hz, 1H).

9b. 4'-Fluoromethylcotinine

Under a nitrogen atmosphere, in a 50 mL round-bottom flask equipped with a rubber septum and a magnetic stir bar were placed product from Example 9a 363 mg (1.76 mmol) and 20 mL of dichloromethane. To this stirring solution, at room temperature, was added 0.248 mL (1.94 mmol) of triethylamine followed by 0.164 mL of methanesulfonyl chloride (2.11 mmol). The reaction mixture was stirred for 30 min. It was then quenched with methanol to destroy excess methanesulfonyl chloride. The reaction mixture was concentrated with a rotary evaporator to obtain a dark yellow oil. This crude material (499 mg, 1.76 mmol) was placed in a 25 mL round-bottomed flask and 7.39 mL (7.39 mmol) of 1M tetra-n-butylammonium fluoride in THF was added to the system. This solution was heated under reflux under nitrogen for 30 minutes. The reaction mixture was concentrated with a rotary evaporator, and the residue was taken up with chloroform. After washing with saturated aqueous sodium bicarbonate solution, the organic layer was dried and concentrated under reduced pressure to give a yellow oil. The crude material was purified by flash column chromatagraphy (50 g of silica gel), eluting with chloroform/methanol (100:3) to provide 131 mg (36% yield) of the title compound as light yellow oil. MS M/Z (DCl/NH3): 209 (M+H)+, 226 (M+NH4)+. $^1$H NMR (CDCl3) δ:2.36 (d, J=9.0, 15 Hz, 1H), 2.42–2.58 (m, 1H), 2.71 (s, 3H), 2.74 (dd, J=9.0, 15 Hz, 1H), 4.52 (d, J=5.2 Hz, 1H), 4.48 (ddd, J=2.6, 5.1, 47 Hz, 2H), 7.47 (dd, J=5.2, 7.7 Hz, 1H), 7.66 (dt, J=1.9, 8.1 Hz, 1H), 8.57 (d, J=1.1 Hz, 1H), 8.66 (m, 1H).

9c. 3'-Fluoromethylnicotine

The product of Example 9a (131 mg, 0.62 mmol) in 10 mL of tetrahydrofuran was treated dropwise with 1M solution of borane (1.25 mL, 1.25 mmol) in tetrahydrofuran at room temperature. After reflux for 3 hours, the reaction was quenched by addition of a large excess of methanol. The resultant solution was allowed to stir at room temperature for an additional 15 minutes. Solvent was then removed under reduced pressure to give a white solid. The crude reaction product was dissolved in 12 mL of methanol and treated with 0.4 mL of 6N aqueous hydrochloric acid. After the pH of the solution was adjusted to 12.0 by addition of 15% aqueous sodium hydroxide solution, the solvent was concentrated in vacuo. The resultant crude product was purified by flash column chromatography on silica gel eluting with acetone/hexane (1:1) to give 59 mg of the title compound (49% for 2 steps) as a colorless oil. MS M/Z (DCl/NH3): 195 (M+H)+, 212 (M+NH$_4$)+. $^1$H NMR (CDCl$_3$))d: 1.70–1.82 (m, 1H), 2.15 (s, 3H), 2.16–2.20 (m, 1H), 2.32–2.45 (m, 2H), 2.97 (d, J=9 Hz, 1H), 3.24 (t, J=9.0 Hz, 1H), 4.47 (ddd, J=4.5, 9.0, 48 Hz, 2H), 7.28 (m, 1H, overlap with CDCl$_3$), 7.72 (dt, J=2.5, 9.0 Hz, 1H), 8.53 (dd, J=2.5, 5.0 Hz, 1H), 8.57 (d, J=2.5, 1H).

9d. 3'-Fluoromethylnicotine oxalate

To the solution of the product from Example 9b in 1.5 mL of diethyl ether was added oxalic acid in 5 mL of diethyl ether dropwise at 0° C. After stirring at 0° C. for 15 minutes, the precipitate was collected by centrifugation, washed with diethyl ether three times and dried in vacuo to yield the title compound as a white powder. MS M/Z (DCl/NH3): 195 (M+H)+, 212 (M+NH$_4$)+. $^1$H NMR (D$_2$O) δ:2.18–2.32 (m, 1H), 2.41–2.58 (m, 1H), 2.82 (s, 3H), 3.07–3.30 (m, 1H), 3.36–3.51 (m, 1H), 4.38–4.74 (m, 2H, overlap with D$_2$O peak), 4.85–4.98 (m, 1H), 7.76 (dd, J=5.0, 7.5 Hz, 1H), 8.26 (d, J=7.5 Hz, 1H), 8.75 (d, J=5.0 Hz, 1H), 8.79 (s, 1H). Anal. calcd. for C$_{11}$H$_{15}$N$_2$F•1.6 C$_2$H$_2$O$_4$•1.0 H$_2$O: C, 47.87; H, 5.71; N, 7.86. Found: C, 47.64; H, 5.43, N, 8.34.

EXAMPLE 10

3'-methylnicotine dioxalate

10a. 4-Phenoxythiocarbonyloxymethylcotinine

Under a nitrogen atmosphere, in a 50 mL round-bottom flask equipped with a rubber septum and a magnetic stir bar were placed 468 mg (2.27 mmol) of 4-(R)hydroxymethylcotinine (product of Example 9a) and 15 mL of dichloromethane. To this stirring solution, at room temperature, was added 0.733 mL (9.0 mmol) of pyridine followed by 0.373 mL of chlorophenoxythiocarbonate (2.72 mmol). The reaction mixture was stirred 0° C.–5° C. for 19 hours and at room temperature for 2 hours, then quenched with methanol to destroy excess acyl chloride. The reaction mixture was concentrated with a rotary evaporator to obtain a dark yellow oil. This crude material was subjected to flash column chromatography (50 g of silica gel), gradually increasing the polarity of the eluent from 2:1 hexane/acetone to 1:1 hexane/acetone to obtain 576 mg (74% yield) of phenoxythiocarbonate as a white solid. MS M/Z (Cl/NH$_3$): 343 (M+H)+, 360 (M+NH$_4$)+. $^1$H NMR (300 MHz, CDCl$_3$) δ:2.43 (dd, J=6, 15 Hz, 1H), 2.68–2.89 (m, 2H), 2.72 (s, 3H), 4.54–4.62 (m, 2H), 4.49 (d, J=6.0 Hz, 1H), 7.06–7.12 (m, 1H), 7.31–7.35 (m, 1H), 7.36–7.48 (m, 3H), 7.59 (dt, J=8.5, 2 Hz, 1H), 8.57 (s, 1H), 8.65 (m, 1H).

10b. 4-Methylcotinine

To a solution of 392 mg (1.14 mmol) of the compound from Step 10a in 15 mL of toluene containing 30 mg (0.38 mmol) of azobis(isobutyronitrile) was added 0.52 mL(1.72 mmol) of tris(trimethylsilyl)silane. The resultant solution was degassed under nitrogen. After 2 hours at 90° C., the toluene was removed under reduced pressure and the residue was allowed to stand on silica gel column for 30 minutes prior to elution with chloroform/methanol, 100:7. There was obtained 246 mg (76%) of the title compound as a colorless oil. MS M/Z (DCl/NH3): 191 (M+H)+, 208 (M+NH$_4$)+. $^1$H NMR (300 MHz, CDCl$_3$) δ:1.19 (d, J=7.5 Hz, 3H), 2.12–2.26 (m, 2H), 2.67 (s, 3H), 2.69–2.83 (m, 1H), 4.11 (d, J=6.0 Hz, 1H), 7.54 (m, 1H), 7.74 (d, J=7.5 Hz, 1H), 8.58 (s, 1H), 8.65 (d, J=4.5 Hz, 1H).

10c. 3'-Methylnicotine

The product of Example 10b (112 mg, 0.59 mmol) in 6 mL of tetrahydrofuran was treated dropwise with 1M solution of borane (1.76 mL, 1.76 mmol) in tetrahydrofuran at room temperature. After reflux for 2 hours, the reaction was quenched by addition of a large excess of methanol. The resultant solution was allowed to stir at room temperature for an additional 15 minutes. Solvent was then removed under reduced pressure to give a white solid. The crude reaction product (110 mg) was dissolved in a mixture of 3 mL of dioxane and 6 mL of ethanol. This reaction mixture was then treated with cesium fluoride (204 mg, 1.76 mmol) as described in Example 1b. The crude product was purified by flash column chromatography on silica gel eluting with hexane/acetone (1:1) to give 22 mg (21% yield for 2 steps) of the title compound as a colorless oil. MS M/Z (DCl/NH3): 177(M+H)+, 194(M+NH$_4$)+. $^1$H NMR (CDCl$_3$) δ:0.98 (d, J=6.0 Hz, 1H), 1.41–1.59 (m, 1H), 1.55–1.79 (m, 1H), 2.16(s, 3H), 2.33–2.50 (m, 1H), 2.59–2.72 (m, 1H), 3.20–3.40 (m, 1H), 3.68–3.74 (m, 1H), 7.25–7.34 (m, 1H, overlap with CDCl$_3$ peak), 7.67–7.83 (m, 1H), 8.50–8.59 (m, 2H).

10d. 3'-Methylnicotine dioxalate

To the solution of the product from Example 10c in 1.5 mL of diethyl ether was added oxalic acid in diethyl ether dropwise at 0° C. After stirring at 0° C. for 15 min, the precipitate was collected by centrifugation, washed with diethyl ether three times and dried in vacuo to yield the title compound as a white powder. MS M/Z (DCl/NH3): 177 (M+H)+, 194 (M+NH$_4$)+. $^1$H NMR (300 MHz, D$_2$O) δ:1.05 (d, J=6.6 Hz, 3H), 1.93–2.09 (m, 1H), 2.41–2.55 (m, 1H), 2.70–2.90 (m, 1H, overlap with 2.83 peak), 2.83 (s, 3H), 3.36–3.52 (m, 1H), 3.84–4.03 (m, 1H), 4.21 (d, J=9.0 Hz, 1H), 8.01 (dd, J=5.5, 9.0 Hz, 1H), 8.49–8.58 (m, 1 Hz), 8.86 (dd, J=1.5, 5.5 Hz, 1H), 8.90 (d, J=3 Hz, 1H). Anal. calcd. for C$_{11}$H$_{16}$N$_2$•2.4 C$_2$H$_2$O$_4$: C, 48.36; H, 5.34; N, 7.14. Found: C, 48.30; H, 5.59; N, 7.24.

EXAMPLE 11

4'-(S)-Cyanonicotine dioxalate

11a. 4'-(R)-Methanesulfonyloxynicotine

Under a nitrogen atmosphere, in a 50 mL round-bottom flask equipped with a rubber septum and a magnetic stir bar were placed product from Example 1b (554 mg, 2.89 mmol) and 20 mL of dichloromethane. To this stirring solution, at room temperature, was added 0.59 mL (4.62 mmol) of triethylamine followed by 0.34 mL of methanesulfonyl chloride (4.34 mmol). The reaction mixture was stirred for 19 hours and then quenched with methanol to destroy excess methanesulfonyl chloride. The reaction mixture was concentrated with a rotary evaporator to obtain a dark yellow oil. This crude material was subjected to flash column chromatography (50 g of silica gel), gradually increasing the polarity of the eluent from 100:5 chloroform/methanol to 100:7 chloroform/methanol, to obtain 420 mg (57% yield) of the methanesulfonate ester as pale yellow viscous oil. MS M/Z (Cl/NH$_3$): 257 (M+H)$^+$, 264 (M+NH$_4$)$^+$. $^1$H NMR (CD$_3$OD) δ:2.24 (s, 3H), 2.65-2.61 (m, 2H), 3.65-3.74 (m, 1H), 3.07 (s, 3H), 3.75-3.85 (m, 1H), 4.25-4.32 (m, 2H), 5.24-5.34 (m, 1H), 7.62 (dd, J=6,7.5 Hz, 1H), 8.09 (d, J=7.5 Hz, 1H), 8.51 (d, J=6 Hz, 1H), 8.59 (s, 1H).

11b. 4′-(S)-cyanonicotine

The product from Example 11a (100 mg, 0.39 mmol) was dissolved in 4 mL of DMF and 190 mg of sodium cyanide was added. This solution was heated at 105° C. under nitrogen for 16 hours. The reaction mixture was concentrated with a rotary evaporator, and the residue was taken up with in chloroform. The crude material was purified by flash column chromatography (50 g of silica gel), eluting with chloroform/methanol (100:0.7) to provide 24 mg (33% yield) of the title compound as yellow oil. MS M/Z (DCl/NH3): 188 (M+H)$^+$, 205 (M+NH$_4$)$^+$. $^1$H NMR (CDCl$_3$) δ:2.02-2.13 (m, 1H), 2.21 (s, 3H), 2.62-2.72 (m, 1H), 3.06-3.16 (m, 1H), 3.21-3.31(m, 1H), 3.51 (d, J=9.2 Hz, 1H), 7.41 (dd, J=4.8,7.7 Hz, 1H), 7.94 (d, J=8.1 Hz, 1H), 8.53-8.60 (m, 2H).

11c. 4′-(S)-Cyanonicotine oxalate

The oil from Example 4b was dissolved in diethyl ether to which was added, dropwise, a solution of oxalic acid (13 mg, 0.14 mmol) in diethyl ether. The resultant precipitate was collected by centrifugation to give 37 mg of the title compound. MS M/Z (DCl/NH3): 188 (M+H)$^+$, 205 (M+NH$_4$)$^+$. $^1$H NMR (D$_2$O) δ:2.60 (s, 3H), 2.60-2.70 (m, 1H), 3.02-3.22 (m, 1H), 3.51 (dd, J=9.2, 12.1 Hz, 1H), 3.75-3.88 (m, 1H), 3.99 (dd, J=3.6, 11.7 Hz, 1H), 4.37 (dd, J=7.7, 10.0 Hz, 1H), 7.84 (ddd, J=0.8, 8.1, 5.2 Hz, 1H), 8.35 (dt, J=1.8, 8.1 Hz, 1H), 8.75 (dd, J=1.4, 5.4 Hz, 1H), 8.78 (d, J=1.5 Hz, 1H). Anal. calcd. for C$_{11}$H$_{13}$N$_3$•2.0 C$_2$H$_2$O$_4$: C, 49.05; H, 4.54; N, 11.49. Found: C, 49.07; H, 4.54; N, 11.49.

EXAMPLE 12

4′-(R)-Acetyloxynicotine oxalate

To a 95 mg (0.53 mmol) sample of 4′-hydroxynicotine (as the borane complex intermediate from Example 1b above) in 3 mL of methylene chloride was added 0.075 mL (0.80 mmol) of acetic anhydride and 0.086 mL (1.06 mmol) of pyridine, and the solution was allowed to stir at room temperature for 16 hours. The solvent was then removed, and the residue was dissolved in 4 mL of ethanol. To this was added 184.2 mg (1.8 mmol) of CsF and the mixture was stirred at 57° C. for 16 hours. The solvent was removed and the residue purified by chromatography on silica gel, eluting with chloroform/methanol (100:7) to give the product as an oil. This was converted to the oxalate salt following the procedure described in Example 1c. MS M/Z (DCl/NH$_3$): 221 (M+H)$^+$, 238 (M+NH$_4$)$^+$. Proton NMR (D$_2$O) δ:2.18 (s, 3H), 2.7-2.9 (m, 2H), 2.94 (s, 3H), 3.61 (d, J=14 Hz, 1H), 4.33 (dd, J=5.5, 14, 1H), 5.04 (q, J=6.2 Hz, 1H), 5.59 (br t, 1H), 8.05 (dd, J=5.5, 8.5, 1H), 8.61 (d, J=8.5 Hz, 1H), 8.88 (d, J=5.5 Hz, 1H), 8.97 (s, 1H). Anal. calcd. for C$_{12}$H$_{16}$N$_2$O$_2$•2.2 C$_2$H$_2$O$_4$: C, 47.09; H, 4.91; N, 6.70. Found: C, 46.96; H, 4.89; N, 6.17.

EXAMPLE 13

3′,4′-Dimethylnicotine oxalate

Step 13a. 3,4-dimethylcotinine

A 124 mg (0.65 mmol) sample of 3-(S)-methylcotinine, from example 4a above, was dissolved in 8 mL of dry THF, and 0.52 mL (0.78 mmol) of LDA was added. The reaction was stirred at −78° C. for 15 min and at 0° C. for 30 min. The temperature was again lowered to −78° C., 0.045 mL (0.72 mmol) of methyl iodide was added and the solution was stirred for 1.5 hours. The reaction was quenched at 0° C. with methanol. The organic solvent was concentrated in vacuo, and the residue was purified by flash column chromatography on silica gel eluting with acetone/hexane (1:1) to give 69 mg of the title product.

Step 13b. 3′,4′-dimethylnicotine

The product of Example 13a was dissolved in 3 mL of THF and 1.0 mL of a 1M solution of borane in tetrahydrofuran was added. The reaction was heated at reflux for 3 hours. The reaction was quenched by stirring with methanol for 10 min, and the solvent was removed. The residue was treated with 118 mg of cesium fluoride in 4 mL of ethanol as described in Example 1b. The crude product was purified by flash column chromatography on silica gel eluting with acetone/hexane (3:4) to give 36 mg of the title compound as a colorless oil. The product was converted to the oxalate salt following the procedure described in Example 1c. MS M/Z (DCl/NH$_3$): 191 (M+H)$^+$, 208 (M+NH$_4$)$^+$. Proton NMR (D$_2$O) δ:0.95 (d, J=6.6, 3H), 1.13 (J=6.9 Hz, 3H), 2.78-2.90 (m, 2H), 2.81 (br s, 3H), 3.05 (br q, 1H), 4.16 (br m, 1H), 4.28 (br m, 1H), 7.90 (m, 1H), 8.40 (dt, J=6, 2 Hz, 1H), 8.82 (m, 2H). Anal calc. for C$_{16}$H$_{22}$N$_2$O$_8$•0.5 H$_2$O: C, 50.66; H, 6.11; N, 7.38; found: C, 51.00; H, 6.02; N, 7.28.

EXAMPLE 14

5′-methylnicotine oxalate

Step 14a. 5′-Hydroxy-5′-methylnicotine

A sample of cotinine (0.95 g, 5.4 mmol, from Aldrich Chemical Co.) was dissolved in 25 mL of anhydrous ether flushed with nitrogen. The solution was cooled to 0° C., and 4.70 mL (6.6 mmol) of methyllithium was slowly added with a syringe. A white precipitate formed, and the mixture was stirred at room temperature for one hour. The reaction was quenched with 10 mL of 1M HCl, then 0.7 g of potassium carbonate was added. The layers were separated, the organic layer removed and the residue dissolved in ethyl acetate. The aqueous layer was extracted overnight with ethyl acetate, and the two fractions were combined, then dried over sodium sulfate and concentrated to leave 1.11 g of a clear orange oil, which was purified on silica gel eluting with chloroform/methanol 20:1 containing 1% ammonium hydroxide, increasing to 7:1 containing 2% ammonium hydroxide. Removal of the solvent gave 0.27 g of the intermediate product.

Step 14b. 5′-methylnicotine oxalate

The 0.27 g (1.4 mmol) of material from step 14a was dissolved in 5.6 mL of anhydrous methanol under an nitrogen atmosphere, and adjusted to the bromcresol green acidic endpoint (yellow) with 2M HCl in anhydrous methanol. To this was added 88 mg (1.4 mmol) of sodium cyanoborohydride, and the pH was again adjusted with the HCl. The reaction was stirred for 0.5 hours and quenched with 6 mL of 0.1M sodium hydroxide. The solution was adjusted to pH 12 with 15% sodium hydroxide solution, then solid sodium chloride and brine was added. The mixture was extracted with ethyl acetate, dried and purified on silica gel, eluting with a series of increasingly polar mixtures of chloroform/methanol containing a small amount of ammonium hydroxide. Two fractions were isolated. Fraction A consisted of 95 mg of the 5'-(S)-methyl isomer. Fraction B consisted of 34 mg of the 5'-(R)-methyl isomer. Each fraction was converted to the oxalate salt following the procedure described in Example 1c.

Fraction A (5'-(S)-isomer): MS M/Z (CDl/NH$_3$): 177 (M+H)+, 194 (M+NH$_4$)+.

Proton NMR (CD$_3$OD) δ:1.53 (d, 3H), 2.05 (m, 1H), 2.35–2.6 (m, 4H), 2.76 (s, 3H). 3.62 (br m, 1H), 4.53 (t, 1H), 7.60 (q, 1H), 8.14 (dt, 1H), 8.67 (dd, 1H), 8.73 (d, 1H).

Fraction B (5'-(R)-isomer): MS M/Z (CDl/NH$_3$): 177 (M+H)+, 194 (M+NH$_4$)+. Proton NMR (CD$_3$OD) δ:1.47 (d, 3H), 1.93–2.07 (m, 1H), 2.4–2.6 (m, 4H), 2.58 (s, 3H), 3.95 (br s, 1H), 7.59 (q, 1H), 8.10 (dt, 1H), 8.67 (dd, 1H), 8.73 (d, 1H).

EXAMPLE 15

5'-Butylnicotine oxalate

Step 15a. 5'-Hydroxy-5'-butylnicotine

Following the procedure of Example 14a, 1.00 g (5.67 mmol) of cotinine was reacted with 2.70 mL (6.75 mmol) of butyl lithium to afford 1.33 g of the title product as an oil.

Step 15b. 5'-Butylnicotine oxalate

Following the procedure of Example 14b, the product of step 15a was reduced with sodium cyanoborohydride. Chromatography provided two fractions, each of which was converted to the oxalate salt as described above.

Fraction A (5'-(S)-isomer): MS M/Z (DCl/NH$_3$): 219 (M+H)+, 236 (M+NH$_4$), 437 (2M+H). Proton NMR (CD$_3$OD) δ:0.96 (m, 3H), 1.35–1.53 (m, 4H), 1.63–1.76 (m, 1H), 1.95–2.13 (m, 2H), 2.35–2.65 (m, 3H), 2.75 (s, 3H), 3.48 (br q, 1H), 4.49 (br t, 1H), 7.58 (q, 1H), 8.14 (dt, 1H), 8.67 (dd, 1H), 8.74 (d, 1H).

Fraction B (5'-(R)-isomer): MS M/Z (DCl/NH$_3$): 219 (M+H)+, 236 (M+NH$_4$)+. Proton NMR (CD$_3$OD) δ:0.97 (m, 3H), 1.35–1.53 (m, 4H), 1.64–1.76 (m, 1H), 1.90–2.05 (m, 2H), 2.45–2.6 (m, 7H), 3.70 (br s, 1H), 7.58 (q, 1H), 8.07 (dt, 1H), 8.67 (dd, 1H), 8.72 (d, 1H).

EXAMPLE 16

4'-(R)-Cyanomethylnicotine oxalate

A 65 mg (0.24 mmol) sample of 4'-(R)-methanesulfonyloxynicotine, from Example 3a above, and 118 mg (2.4 mmol) of NaCN were dissolved in 2.5 mL of DMF and 0.4 mL of water and stirred at 100° C. for 16 hours. The solvent was removed by evaporation, and the residue was purified on a silica gel column, eluting with 1:1 acetone hexane. Removal of the solvent gave 32 mg of free base, which was converted to the oxalate salt as described above. MS M/Z (DCl/NH$_3$): 202 (M+H)+, 219 (M+NH$_4$)+. Proton NMR (D$_2$O) δ:2.5–2.6 (m, 1H), 2.7–2.92 (m, 7H), 3.1–3.2 (m, 1H), 3.21–3.41 (m, 1H), 4.12 (m, 1H), 7.85 (dd, J=8.1, 5.2 Hz, 1H), 8.37 (dt, J=8, 1.6 Hz 1H), 8.78 (dd, J=5.5, 1.5 Hz, 1H), 8.83 (d, J=1.8 Hz, 1H). Anal calc. for C$_{12}$H$_{15}$N$_3$•2 C$_2$H$_2$O$_4$: C, 50.39; H, 5.02; N, 11.02; found: C, 50.54; H, 5.06; N, 11.07.

EXAMPLE 17

3'-Aminonicotine oxalate 17a. 4-Benzyloxycarbonylaminocotinine

To 1.00 g (4.5 mmol) of trans-4-cotininecarboxylic acid (available from Aldrich Chemical Co.) dissolved in 20 mL of toluene was added 0.823 mL (4.73 mmol) of diisopropylethylamine and 0.988 mL (4.6 mmol) of DPPA, and the reaction was stirred at 80° C. for 2 hours. After cooling to room temperature 0.537 mL (5.19 mmol) of benzyl alcohol was added, and the reaction was stirred at room temperature for 16 hours and at 80° C. for 3 hours. The solvent was removed, and the residue was purified by chromatography on silica gel, eluting with 10:7 chloroform:methanol to afford 1.1 g of title compound.

17b. 3'-Benzyloxycarbonylaminonicotine

A 500 mg sample of the compound from step 17a was dissolved in 1.2 mL of THF and 4.65 mL of BH$_3$ was added. The reaction was heated at reflux for 2 hours, then concentrated and quenched with methanol. The borane complex was decomposed by reaction with CsF in ethanol as described in Example 1b above to afford 152 mg of title compound.

17c. 3'-Aminonicotine

A 110 mg sample of 3'-benzyloxycarbonylaminonicotine, from step 17b above, was dissolved in 10 mL of ethanol and stirred under hydrogen for 16 hours. The solvent was evaporated, and the residue was purified by chromatography on silica gel, eluting with 10:1, then 20:3, chloroform:methanol, to afford after drying 40 mg of the title compound. MS M/Z (DCl/NH$_3$): 178 (M+H). Proton NMR (D$_2$O) δ: 2.59 (s, 3H), 2.6–2.68 (m, 1H), 2.8–2.94 (m, 2H), 3.08–3.2 (m, 2H), 7.21–7.33 (m, 1H), 7.50 (dt, J=7.5, 2 Hz), 1H), 8.46 (d, J=2, 1H), 8.52 (dd, J=2, 4.5, 1H).

EXAMPLE 18

3'-Methylaminonicotine oxalate

A sample of 3'-aminonicotine, from Example 17 above, is dissolved in a 1:1 mixture of formic acid:formaldehyde and heated at 80° C. for 16 hours. The excess reagents are removed by evaporation in vacuo, and the residue is purified by chromatography on silica gel, eluting with 5–10% methanol in methylene chloride. The product is converted to the oxalate salt as described in Example 1c above.

EXAMPLE 19

4'-(R)-Methanesulfonyoxynicotine oxalate 19a. 3-(R)-Methanesulfonyloxycotinine A 750 mg (13.90 mmol) sample of 3-(R)-hydroxycotinine, from Example 1a above, was dissolved in 20 mL of methylene chloride and 0.262 mL of methanesulfonyl chloride and 0.998 mL of triethylamine were added. The reaction was stirred at room temperature for 16 hours. The solvent was removed, the residue dissolved in chloroform and the product purified by chromatography on silica gel, eluting with 100:6 chloroform:methanol. Removal of the solvent and drying gave 689 mg of the title product.

19b. 4'-(R)-Methanesulfonyloxynicotine

To the product of Example 19a (652 mg, 2.41 mmol) in 15 mL of THF was added under nitrogen and dropwise over a period of 5 minutes 6.03 mL (6.03 mmol) of a 1M solution of borane in THF. After stirring under reflux for 2 hours, methanol was added dropwise and the reaction stirred for an additional hour. The solvent was then removed in vacuo, affording a white solid borane complex. A 312 mg sample of the borane complex was dissolved in anhydrous ethanol. To this was added 334 mg of cesium fluoride, and the resultant solution was stirred under reflux overnight. Evaporation of the solvent provided a white solid which was purified on a silica gel column, eluting with chloroform-:methanol (10:7) to give 117 mg of the product.

19c. 4'-(R)-Methanesulfonyloxynicotine oxalate

Following the procedure of Example 1c above, a 35 mg sample of the oxalate salt was prepared. MS M/Z (DCl/NH3): 257 (M+H)+. $^1$H NMR (D$_2$O) δ: 2.85 (m, 5H), 3.35 (s, 3H), 3.77 (d, J=14 Hz, 1H), 4.38 (dd, J=5.5, 13, 1H), 5.0 (m, 1H), 5.7 (m, 1H), 7.87 (m, 1H), 8.37 (dt, J=8, 1.5 Hz, 1H), 8.79 (m, 1H), 8.82 (m, 1H). Anal. calcd for $C_{11}H_{16}N_2O_3S \bullet 2\ C_2H_2O_4 \bullet 0.3\ Et_2O$: C, 44.43; H, 5.05; N, 6.11. Found: C, 42.55; H, 4.71; N, 6.49.

EXAMPLE 20

4'-Thiomethylnicotine oxalate

Following the procedure of *Bull. Soc. Chim. Belg.*, 1979, 87: 223, 229, 299, 525, cotinine is reacted with Lawesson's reagent under nitrogen and anhydrous conditions to convert the oxo group to a thioxo group. This thioxocotinine is reacted under anhydrous, inert conditions with the ylide, methoxymethyltriphenylphosphonium bromide (Aldrich), to convert the compound into the 5'-hydroxymethylenenicotine, which is hydrolyzed to the nicotine-5'-aldehyde with mild acid. The aldehyde is then reduced to the 5'-hydroxymethylnicotine by treatment with sodium borohydride in ethanol. Following the procedure of Example 8, the 5'-hydroxymethylnicotine is reacted with methanesulfonyl chloride, then the resulting mesylate compound is reacted with sodium sulfide, and the resulting product is converted to the oxalate salt to afford the title compound.

EXAMPLE 21

4'-Thiocyanatomethylnicotine oxalate

Following the procedure of *Bull. Soc. Chim. Belg.* 87: 223, 229, 299, 525 (1979), cotinine is reacted with Lawesson's reagent under nitrogen and anhydrous conditions to convert the oxo group to a thioxo group. This thioxocotinine is reacted under anhydrous, inert conditions with the ylide, methoxymethyltriphenylphosphonium bromide (Aldrich), to convert the compound into the 5'-hydroxymethylenenicotine, which is hydrolyzed to the nicotine-5'-aldehyde with mild acid. The aldehyde is then reduced to the 5'-hydroxymethylnicotine by treatment with sodium borohydride in ethanol. Following the procedure of Example 8, the 5'-hydroxymethylnicotine is reacted with methanesulfonyl chloride, then the resulting mesylate compound is reacted with sodium cyanate, and the resulting product is converted to the oxalate salt to afford the title compound.

EXAMPLE 22

5'-Fluoromethylnicotine oxalate

Nicotine 5'-carboxylic acid (prepared as described by Hellmann (*Justus Liebig's Ann. Chem.*, 1960, 672:97–102)) is reduced with lithium aluminun hydride to give the corresponding alcohol, 5'-hydroxymethylnicotine. Following the procedure of Example 8, the 5'-hydroxymethylnicotine is reacted with methanesulfonyl chloride, then the resulting mesylate compound is reacted with tetrabutylammonium fluoride, and the resulting product is converted to the oxalate salt to afford the title compound.

EXAMPLE 23

5'-Cyanomethylnicotine oxalate

Nicotine 5'-carboxylic acid (prepared as described by Hellmann (*Justus Liebig's Ann. Chem.*, 1960, 672:97–102)) is reduced with lithium aluminun hydride to give the corresponding alcohol, 5'-hydroxymethylnicotine. Following the procedure of Example 8, the 5'-hydroxymethylnicotine is reacted with methansulfonyl chloride, then the resulting mesylate compound is reacted with sodium cyanide according to the procedure of Example 16, and the resulting product is converted to the oxalate salt to afford the title compound.

EXAMPLE 24

3',5'-Dimethylnicotine oxalate

Following the procedure of Example 14, a sample of 4-(S)-methylcotinine, from Example 10a, is reacted with methyllithium, and the resulting product is converted to the oxalate salt to afford the title compound.

EXAMPLE 25

4',5'-Dimethylnicotine oxalate

Following the procedure of Example 14, a sample of 3-(S)-methylcotinine, from Example 4a, is reacted with methyllithium, and the resulting product is converted to the oxalate salt to afford the title compound.

EXAMPLE 26

4'-Fluoromethyl-3'-methylnicotine oxalate

Following the procedure of Example 7a, sample of 3-(S)-methylcotinine is reacted with lithium diisopropyl amide to form 4-hydroxymethyl-3-methylcotinine. Following the procedure of Example 8, 4-hydroxymethyl-3-methylcotinine is reacted with methansulfonyl chloride, then the resulting mesylate compound is reacted with tetrabutylammonium fluoride, and the resulting product is converted to the oxalate salt to afford the title compound.

EXAMPLE 27

3'-Fluoromethyl-4'-methylnicotine oxalate

Following the procedure of Example 4a, a sample of 4-(S)-fluoromethylcotinine, from example 9, is reacted with lithium with lithium diisopropyl amide then methyl iodide to give the 4-(S)-fluoromethyl-3-methylcotinine. Following the procedure of Example 9c, the 4-(S)-fluoromethyl-3-methylcotinine is then reduced with borane in THF, and the resulting borane complex is decomposed with CsF to provide the 3'-(S)-fluoromethyl-4'-methylnicotine, and the resulting product is converted to the oxalate salt to afford the title compound.

EXAMPLE 28

5'-Fluoromethyl-4'-methylnicotine oxalate

Following the procedure of *Bull. Soc. Chim. Belg.* 87: 223, 229, 299, 525 (1979), 3-methylcotinine is reacted with Lawesson's reagent under nitrogen and anhydrous conditions to convert the oxo group to a thioxo group.

This thioxo cotinine is reacted under anhydrous, inert conditions with the ylide, methoxymethyltriphenylphosphonium bromide (Aldrich), to convert the compound into the 5'-hydroxymethylene-4'-methylnicotine, which is hydrolyzed to the 4'-methylnicotine-5'-aldehyde with mild acid. The aldehyde is then reduced to the 5'-hydroxymethyl-4'-methylnicotine by treatment with sodium borohydride in ethanol. Following the procedure of Example 8, the 5'-hydroxymethyl-4'-methylnicotine is reacted with methansulfonyl chloride, then the resulting mesylate compound is reacted with tetrabutylammonium fluoride, and the resulting product is converted to the oxalate salt to afford the title compound.

What is claimed is:

1. A compound having the formula:

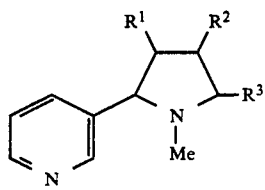

including pharmaceutically-acceptable salts or prodrugs thereof, wherein:

$R^1$ is
   hydrogen,
   fluorine,
   fluoromethyl,
   cyanomethyl, or
   cyano;
$R^2$ is
   hydrogen,
   fluorine,
   fluoromethyl,
   fluorobenzyl,
   cyanomethyl, or
   cyano;
$R^3$ is
   hydrogen, or
   fluoromethyl;
with the requirement that not all of $R^1$, $R^2$ and $R^3$ are concurrently hydrogen.

2. A compound according to claim 1, in which $R^1$ and $R^2$, or $R^2$ and $R^3$, or $R^1$ and $R^3$ are hydrogen, and the third substituent is not hydrogen.

3. A compound according to claim 1, which is selected from:
   4'-Fluoronicotine,
   4'-Fluoromethylnicotine,
   3'-Fluoromethylnicotine,
   4'-Cyanonicotine,
   4'-Cyanomethylnicotine, and
   5'-Fluoromethylnicotine,
or a pharmaceutically-acceptable salt or prodrug thereof.

4. A compound according to claim 3, which is:
   4'-Fluoronicotine,
   4'-Fluoromethylnicotine,
or a pharmaceutically-acceptable salt or prodrug thereof.

5. A pharmaceutical composition comprising a pharmaceutically-acceptable carrier and a therapeutically-effective amount of a compound according to claim 1.

6. A pharmaceutical composition according to claim 5 for treating cognitive, neurological and mental disorders characterized by decreased cholinergic function.

7. A method for selectively activating neuronal nicotinic acetylcholine receptors comprising administering to a patient in need of such treatment a therapeutically-effective amount of a compound according to claim 1.

8. A method for treating dementias, attentional hyperactivity disorder, anxiety associated with cognitive impairment, or substance abuse withdrawal characterized by decreased cholinergic function comprising administering to a patient in need of such treatment a therapeutically-effective amount of a compound according to claim 1.

* * * * *